(12) United States Patent
Walsh et al.

(10) Patent No.: US 11,931,735 B2
(45) Date of Patent: *Mar. 19, 2024

(54) METHODS AND APPARATUS FOR MANUFACTURING A MICROFLUIDIC ARRANGEMENT, AND A MICROFLUIDIC ARRANGEMENT

(71) Applicant: Oxford University Innovation Limited, Oxford (GB)

(72) Inventors: Edmond Walsh, Oxford (GB); Alexander Feuerborn, Oxford (GB); Peter Richard Cook, Oxford (GB); Cristian Soitu, Oxford (GB)

(73) Assignee: Oxford University Innovation Limited, Oxford (GB)

( * ) Notice: Subject to any disclaimer, the term of this patent is extended or adjusted under 35 U.S.C. 154(b) by 837 days.

This patent is subject to a terminal disclaimer.

(21) Appl. No.: 16/970,920

(22) PCT Filed: Feb. 5, 2019

(86) PCT No.: PCT/GB2019/050303
§ 371 (c)(1),
(2) Date: Aug. 18, 2020

(87) PCT Pub. No.: WO2019/162644
PCT Pub. Date: Aug. 29, 2019

(65) Prior Publication Data
US 2020/0376486 A1 Dec. 3, 2020

(30) Foreign Application Priority Data

Feb. 21, 2018 (GB) ........................................ 1802819
Jul. 23, 2018 (GB) ........................................ 1811977

(51) Int. Cl.
*B01J 19/00* (2006.01)
*B01L 3/00* (2006.01)
(Continued)

(52) U.S. Cl.
CPC ..... *B01L 3/502707* (2013.01); *B01J 19/0046* (2013.01); *B01L 3/0293* (2013.01);
(Continued)

(58) Field of Classification Search
CPC ............. B01L 3/502707; B01L 3/0293; B01L 3/502769; B01L 3/5088; B01L 2200/0642;
(Continued)

(56) References Cited

U.S. PATENT DOCUMENTS 7,189,580 B2 3/2007 Beebe et al.
8,053,249 B2 11/2011 Beebe et al.
(Continued)

FOREIGN PATENT DOCUMENTS

CN 105142790 A 12/2015
EP 1 527 888 A2 5/2005
(Continued)

OTHER PUBLICATIONS

Barnes et al., "Chapter 2: Capillarity and the mechanics of surfaces", Interfacial Science: An Introduction—Interfacial Science, Feb. 2011, pp. 10-42.
(Continued)

*Primary Examiner* — Jill A Warden
*Assistant Examiner* — John McGuirk
(74) *Attorney, Agent, or Firm* — Foley & Lardner LLP

(57) ABSTRACT

Methods and apparatus for manufacturing a microfluidic arrangement are disclosed. In one arrangement, a continuous body of a first liquid is provided in direct contact with a first substrate. A second liquid covers the first liquid. A separa-
(Continued)

tion fluid, immiscible with the first liquid, is propelled through at least the first liquid and into contact with the first substrate along all of a selected path on the surface of the first substrate. First liquid that was initially in contact with all of the selected path is displaced away from the selected path. The first liquid is divided to form sub-bodies of first liquid that are separated from each other. For each of one or more of the sub-bodies, a sub-body footprint represents an area of contact between the sub-body and the first substrate, and all of a boundary of the sub-body footprint is in contact with a closed loop of the selected path surrounding the sub-body footprint.

26 Claims, 13 Drawing Sheets

(51) Int. Cl.
    *B01L 3/02* (2006.01)
    *C12M 1/32* (2006.01)
    *C12M 3/06* (2006.01)
(52) U.S. Cl.
    CPC ....... *B01L 3/502769* (2013.01); *B01L 3/5088* (2013.01); *C12M 23/12* (2013.01); *C12M 23/16* (2013.01); *B01J 2219/00531* (2013.01); *B01J 2219/00617* (2013.01); *B01J 2219/00621* (2013.01); *B01J 2219/00659* (2013.01); *B01J 2219/00743* (2013.01); *B01L 2200/0642* (2013.01); *B01L 2200/12* (2013.01); *B01L 2300/0816* (2013.01); *B01L 2300/161* (2013.01); *B01L 2400/0442* (2013.01)
(58) Field of Classification Search
    CPC ......... B01L 2200/12; B01L 2300/0816; B01L 2300/161; B01L 2400/0442; B01L 7/52; B01L 3/502784; B01L 3/5027; B01L 2300/0819; B01L 2300/0829; B01L 2300/0861–0896; B01L 2300/16; B01L 2400/00; B01J 19/0046; B01J 2219/00531; B01J 2219/00617; B01J 2219/00621; B01J 2219/00659; B01J 2219/00743; B01J 2219/0072; C12M 23/12; C12M 23/16; C12M 1/00
    See application file for complete search history.

(56) References Cited

U.S. PATENT DOCUMENTS

| | | | |
|---|---|---|---|
| 8,168,133 | B2 | 5/2012 | Beebe et al. |
| 8,361,782 | B2 | 1/2013 | Pugia et al. |
| 8,652,852 | B2 | 2/2014 | Beebe et al. |
| 8,985,547 | B2 | 3/2015 | Weibel et al. |
| 9,707,560 | B2 | 7/2017 | Muelleder et al. |
| 2006/0263241 | A1 | 11/2006 | Beebe et al. |
| 2010/0093109 | A1 | 4/2010 | Pugia et al. |
| 2010/0116343 | A1 | 5/2010 | Weibel et al. |
| 2013/0037115 | A1 | 2/2013 | Beebe et al. |
| 2015/0034163 | A1* | 2/2015 | Abate .................. B01F 23/41 137/888 |
| 2016/0059232 | A1 | 3/2016 | Muelleder et al. |
| 2016/0096153 | A1* | 4/2016 | Lee .................. B01F 33/3022 366/167.1 |

FOREIGN PATENT DOCUMENTS

| | | |
|---|---|---|
| GB | 2 543 616 A | 4/2017 |
| GB | 2 543 618 A | 4/2017 |
| GB | 2 544 152 A | 5/2017 |
| JP | 2010-526293 A | 7/2010 |
| JP | 5296054 B2 | 7/2010 |
| JP | 2010-531971 A | 9/2010 |
| JP | 5236667 B2 | 9/2010 |
| WO | WO-2006/121667 A2 | 11/2006 |
| WO | WO-2008/127818 A2 | 10/2008 |
| WO | WO-2014/172740 A1 | 10/2014 |
| WO | WO-2016133783 A1 * | 8/2016 |
| WO | WO-2017/064514 A1 | 4/2017 |
| WO | WO-2018/033692 A1 | 2/2018 |

OTHER PUBLICATIONS

Berthier et al., "Flow rate analysis of a surface tension driven passive micropump", Lab Chip, vol. 7, 2007, pp. 1475-1478.
Berthuy et al., "Cells on chip for multiplex screening", Biosensors and Bioelectronics, vol. 76, 2016, pp. 29-37.
Bonn et al., "Wetting and spreading", Reviews of Modern Physics, vol. 81, Apr.-Jun. 2009, pp. 739-805.
Boys, "Soap-Bubbles," Their Colours and the Forces Which Mould Them, The Romance of Science, 12th Thousand, Enlarged Edition, The Macmillan Company, 1920, 202 pages.
Cate, et al., "Recent Developments in Paper-Based Microfluidic Devices", Analytical Chemistry, vol. 87, 2015, pp. 19-41.
Du, et al., "Cell-Based Drug Combination Screening with a Microfluidic Droplet Array System", Analytical Chemistry, vol. 85, 2013, pp. 6740-6747.
Duocastella et al., "Film-free laser forward printing of transparent and weakly absorbing liquids", Optics Express, vol. 18, No. 21, Oct. 11, 2010, 11 pages.
Fletcher et al., "Theoretical considerations of chemical reactions in micro-reactors operating under electroosmotic and electrophoretic control", Analyst, vol. 124, 1999, pp. 1273-1282.
Garcia-Cordero et al., "Sessile droplets for chemical and biological assays", Lab Chip, vol. 17, 2017, pp. 2150-2166.
Gau et al., "Liquid Morphologies on Structured Surfaces: From Microchannels to Microchips", Science, vol. 283, Jan. 1, 1999, 5 pages.
Hancock et al., "Surface-Tension-Driven Gradient Generation in a Fluid Stripe for Bench-Top and Microwell Applications", Small, vol. 7, No. 7, Apr. 4, 2011, pp. 892-901.
Hoffman et al., "Solid-phase PCR in a picowell array for immobilizing and arraying 100,000 PCR products to a microscope slide", Lab Chip, vol. 12, 2012, pp. 3049-3054.
Javadi et al., "Effect of wetting on capillary pumping in microchannels", Scientific Reports, vol. 3, No. 1412, 2013, 6 pages.
Ju et al., "Backward flow in a surface tension driven micropump", Journal of Micromechanics and Microengineering, vol. 18, 2008, 5 pages.
Kolesky et al., "3D Bioprinting of Vascularized, Heterogeneous Cell-Laden Tissue Constructs", Advanced Materials, vol. 26, 2014, pp. 3124-3130.
Kolesky et al., "Three-dimensional bioprinting of thick vascularized tissues", PNAS, vol. 113, No. 12, 2016, pp. 3179-3184.
Lam et al., "Surface-Tension-Confined Microfluidics", Langmuir, vol. 18, 2002, pp. 948-951.
Lee et al., "Wall-less liquid pathways formed with three-dimensional microring arrays", Applied Physics Letters, vol. 101, 2012, 5 pages.
Lee et al., "Wall-less Microfluidic Channels Using 3-Dimensional Ring Arrays ", 16th International Conference on Minaturized Systems for Chemistry and Life Sciences, Oct. 28-Nov. 1, 2012, pp. 296-298.
Lee et al., Capillary Based Patterning of Cellular Communities in Laterally Open Channels, Analytical Chemistry, vol. 82, 2010, pp. 2900-2906.
Liberski et al., "One Cell-One well": a New Approach to Inkjet Printing Single Cell Microarrays, ACS Combinatorial Science, vol. 13, 2011, pp. 190-195.
Liu et al., "A generalized formula for inertial lift on a sphere in microchannels", Lab Chip, vol. 16, 2016, pp. 884-892.
Love et al., "A microengraving method for rapid selection of single cells producing antigen-specific antibodies", Nature Biotechnology, vol. 24, No. 6, Jun. 2006, pp. 703-707.

(56) References Cited

OTHER PUBLICATIONS

MacLeod et al., "A Growing-Drop Technique for Measuring Dynamic Interfacial Tension", Journal of Colloids and Interface Science, vol. 160, No. 2, Oct. 1993, pp. 435-448.
Marcy et al., "Dissecting biological "dark matter" with single-cell genetic analysis of rare and uncultivated TM7 microbes from the human mouth", PNAS, vol. 104, No. 29, Jul. 17, 2007, pp. 11889-11894.
Memic et al., Research Highlights, Lab Chip, vol. 13, 2013, pp. 4157-4159.
Oliveira et al., "Two-Dimensional Open Microfluidic Devices by Tuning the Wettability on Patterned Superhydrophobic Polymeric Surface", Applied Physics Express, vol. 3, 2010, 4 pages.
Parekh et al., "3D printing of liquid metals as fugitive inks for fabrication of 3D microfluidic channels", Lab Chip, vol. 16, 2016, pp. 1812-1820.
Pique et al., "Direct writing of electronic and sensor materials using a laser transfer technique", Journal of Materials Research, vol. 15, No. 9, Sep. 2000, pp. 1872-1875.
Prakadan et al., "Scaling by shrinking: empowering single-cell 'omics' with microfluidic devices", Nat. Rev. Genet., vol. 18, No. 6, Jun. 2017, pp. 345-361.
Rahmanian et al., "Pen microfluidics: rapid desktop manufacturing of sealed thermoplastic microchannels," Lab Chip, vol. 13, No. 6, 2013, pp. 1102-1108.
Sackmann et al., "The present and future role of microfluidics in biomedical research", Nature, vol. 507, Mar. 13, 2014, 181-189.
Schmitz, et al., "Dropspots: a picoliter array in a microfluidic device", Lab Chip, vol. 9, No. 1, 2009, pp. 44-49.
Schutzius et al., "Surface tension confined (STC) tracks for capillary-driven transport of low surface tension liquids", Lab Chip, vol. 12, 2012, pp. 5237-5242.
Setu et al., "Superconfinement tailors fluid flow at microscales", Nature Communications, vol. 6, Jun. 15, 2015, 8 pages.
Shembekar et al., "Droplet-based microfluidics in drug discovery, transcriptomics and high-throughput molecular genetics", Lab Chip, vol. 16, 2016, pp. 1314-1331.
Shemesh et al., "Stationary nanoliter droplet array with a substrate of choice for single adherent/nonadherent cell incubation and analysis", PNAS, vol. 111, No. 31, Aug. 5, 2014, pp. 11293-11298.
Sousa et al., "Patterned superhydrophobic paper for microfluidic devices obtained by writing and printing", Cellulose. vol. 20, 2013, pp. 2185-2190.
Speth et al., "Capillary instability on a hydrophilic stripe", New Journal of Physics, vol. 11, 2009, 16 pages.
Straub, "The Role of Surface Tension for Two-Phase Heat and Mass Transfer in the Absence of Gravity", Experimental Thermal and Fluid Science, vol. 9, 1994, pp. 253-273.
Sugden, "The Determination of Surface Tension from the Maximum Pressure in Bubbles", J. Chem. Soc. Trans., vol. 121, 1922, pp. 858-866.
Sun et al., "A novel picoliter droplet array for parallel real-time polymerase chain reaction based on double-inkjet printing", Lab Chip, vol. 14, 2014, pp. 3603-3610.
Sun et al., "Droplet-in-oil array for picoliter-scale analysis based on sequential inkjet printing", Lab Chip, vol. 15, 2015, pp. 2429-2436.
Tan et al., "Microfluidic mixing in a Y-junction open channel", AIP Advances, vol. 2, 2012, 12 pages.
Tan et al., "Stability of flowing open fluidic channels", AIP Advances, vol. 3, 2013, 13 pages.
Tseng et al., "Research highlights: printing the future of microfabrication", Lab Chip, vol. 14, 2014, pp. 1491-1495.
Walker et al., "A passive pumping method for microfluidic devices", Lab Chip, vol. 2, 2002, pp. 131-134.
Walsh et al., "Microfluidics with fluid walls", Nature Communications, vol. 8, No. 816, 2017, 9 pages.
You et al., "Surface-Tension-Confined Microfluidics and Their Applications", ChemPhysChem, vol. 14, 2013, pp. 471-481.
Zhu et al., "Nanoliter-Scale Protein Crystallization and Screening with a Microfluidic Droplet Robot", Scientific Reports, vol. 4, 2014, 9 pages.
Zhu et al., "Printing 2-Dimentional Droplet Array for Single-Cell Reverse Transcription Quantitative PCR Assay with a Microfluidic Robot", Scientific Reports, vol. 5, 2015, 7 pages.
Hartmann, et al., "Non-contact protein microarray fabrication using a procedure based on liquid bridge formation", (2009) Analytical and Bioanalytical Chemistry, vol. 393, No. 2, pp. 591-598 (abstract only, 1 page).

* cited by examiner

METHODS AND APPARATUS FOR MANUFACTURING A MICROFLUIDIC ARRANGEMENT, AND A MICROFLUIDIC ARRANGEMENT

CROSS-REFERENCE TO RELATED APPLICATIONS

This application is a U.S. national stage application under 35 U.S.C. § 371 claiming the benefit of International Patent Application No. PCT/GB2019/050303, filed Feb. 5, 2019, which claims priority to GB Application No. 1802819.1, filed Feb. 21, 2018 and GB Application No. 1811977.6, filed Jul. 23, 2018, the entire contents of each of which are incorporated by reference in their entireties.

The invention relates to creating a microfluidic arrangement by dividing a body of a first liquid into a plurality of separated sub-bodies. The sub-bodies can be used to provide isolated samples, or microfluidic circuits with liquid walls, containing material to be investigated, such as living cells or other biological material.

Microwell plates are widely used for studies involving biological material. Miniaturisation of the wells allows large numbers of wells to be provided in the same plate. For example, plates having more than 1000 wells, each having a volume in the region of tens of nanolitres, are known. Further miniaturisation is difficult, however, due to the intrinsic need to provide solid walls that separate the wells from each other. The thickness of these walls reduces the surface area available for the wells. For a typical plate having 1536 wells, for example, the walls would be expected to occupy about 60% of the available surface for current designs. For higher densities the proportion of the surface area made unavailable by the walls will increase further.

A further obstacle to miniaturisation of microwell plates is the difficulty of adding liquids to small wells defined by physical walls. For liquid to be added reliably to a well (i.e. in a way which avoids trapping of air beneath the liquid), a tip needs to be advanced accurately to the bottom of the well without the tip or any liquid attached to the tip touching the walls of the well. If contact is made with the walls before the liquid reaches the bottom of the well it is likely that a meniscus will form with the wall and trap air beneath the liquid. This may mean that liquid cannot reach the bottom of the well.

Microwell plates also lack flexibility because the size of the wells and the number of wells per plate is fixed. Furthermore, biological and chemical compatibility can be limited by the need to use a material that can form the structures corresponding to the wells in an efficient manner. For example, for high density plates it may be necessary to use a material such as polydimethylsiloxane (PDMS), but untreated PDMS has poor biological and chemical compatibility because it leaches toxin and reacts with organic solvents.

EP 1 527 888 A2 discloses an alternative approach in which ink jet printing is used to form an array of closely spaced droplets of growth medium for culture and analysis of biological material. This approach provides more flexibility than a traditional microwell plate but requires sophisticated equipment to perform the printing. Additionally, it is time consuming to add further material to the droplets after the droplets have been formed and there is significant footprint not wetted by the resultant sessile drops as they do not tessellate.

It is an object of the invention to provide an alternative way of creating a microfluidic arrangement that at least partially addresses one or more of the challenges discussed above.

According to an aspect of the invention, there is provided a method of manufacturing a microfluidic arrangement, comprising: providing a continuous body of a first liquid in direct contact with a first substrate; providing a second liquid in direct contact with the continuous body of first liquid and covering the continuous body of first liquid; and propelling a separation fluid, immiscible with the first liquid, through at least the first liquid and into contact with the first substrate along all of a selected path on the surface of the first substrate, thereby displacing first liquid that was initially in contact with all of the selected path away from the selected path without any solid member contacting the selected path directly and without any solid member contacting the selected path via a globule of liquid held at a tip of the solid member, the selected path being such that the continuous body of the first liquid is divided to form a single sub-body of first liquid separated from the rest of the continuous body of first liquid by the second liquid or a plurality of sub-bodies of first liquid separated from each other by the second liquid, wherein: for each of one or more of the sub-bodies, a sub-body footprint represents an area of contact between the sub-body and the first substrate, and all of a boundary of the sub-body footprint is in contact with a closed loop of the selected path surrounding the sub-body footprint.

The method allows sub-bodies of a liquid to be formed flexibly on a substrate without any mechanical or chemical structures being provided beforehand to define the geometry of the sub-bodies. The shapes and sizes of the sub-bodies are defined by the geometry of the selected path, which defines the area on the first substrate where the first liquid has been displaced. The second liquid fills the space left by the first liquid and isolates the sub-bodies from each other. As described below, the choice of the selected path is relatively unrestricted. It is possible to create extremely small sub-bodies, for example of the order of 100 microns or smaller, which would be difficult or impossible to create at reasonable cost and/or time, without surface modification/treatment, using standard microwell plate manufacturing techniques. The sub-bodies can also be positioned much closer to each other than is possible using microwell plates with physical walls. The liquid walls of embodiments of the present disclosure typically have a thickness of 70-120 microns (and can be created at thicknesses down to around 15 microns), which allows more than 90% of the surface area of the microfluidic arrangement to be available for containing liquids to be manipulated. Furthermore, there are no solid walls to interfere with adding further liquid to any of the sub-bodies.

In comparison with arrays of droplets deposited by ink jet printing or the like, the method avoids the need for sophisticated printing equipment and can achieve higher space filling efficiency (because the shapes of the sub-bodies do not need to be circular). Materials to be investigated (e.g. biological material such as cells, DNA, proteins, or other molecules of interest such a constituents of liquid crystals) and test substances (e.g. drugs) can be added to multiple sub-bodies simultaneously by adding them to the continuous body of the first liquid before it is divided into the sub-bodies. Concentration gradients can be imposed in strips of the first liquid and the strips can be divided into sub-bodies to quickly and easily create multiple samples containing different concentrations of components. The inventors have furthermore found that depositing fluid (and cells, etc.) into the sub-bodies after they have been formed can be achieved more efficiently (merging occurs more quickly) for sub-bodies that do not have a round footprint (e.g. substantially square or rectangular sub-bodies). Without wishing to be bound by theory, it is thought this effect may be influenced by the reduced symmetry of the non-circular sub-bodies and/or by the fact that they can be flatter. Non-circular sub-bodies can be formed easily using methods of the disclosure.

In an embodiment, the separation fluid is propelled onto the selected path on the first substrate by pumping the separation fluid from a distal tip of an injection member while moving the distal tip relative to the first substrate. This approach can be implemented using relatively simple hardware in a cost-effective and reliable manner. Alternative approaches which involve contact of a solid member with the selected path (e.g. using scraping of the solid member along the selected path), require a degree of clearance to be provided in a mounting arrangement of the solid member to allow for movement of the solid member perpendicular to the surface of the first substrate (i.e. in the z-direction). In comparison to such approaches, the present approach can provide higher resolution because no movement of the injection member perpendicular to the surface of the first substrate (z-direction) is required. The injection member can thus be clamped rigidly without any clearance in directions parallel to the surface of the first substrate (x-y directions), which improves positioning accuracy. Positioning accuracy will be limited only by the accuracy of the mechanism used to move the injection member over the first substrate. The removal of the need for contact between the injection member and the first substrate also means that the approach is less sensitive to errors caused by height variations in the surface of the first substrate and/or does not need to compensate for such height variations. The absence of required z-direction movement also improves speed relative to alternative approaches which involve contact of a solid member with the selected path (where time-consuming z-direction movement is required).

The use of a separation fluid propelled onto the surface of the substrate also provides enhanced flexibility relative to alternative approaches which involve contact of a solid member with the selected path. Where a solid member is used to cut through the first liquid along a selected path, the width of the cut is defined by the fixed size and shape of the solid member. If a different sized cut is required it would be necessary to replace the solid member with a different solid member. Furthermore, manufacturing errors in the solid member will lead to corresponding errors in the width of cut. In the present approach, in contrast, the width of the cut can be varied by altering the way the separation fluid is propelled onto the surface, for example by altering the velocity of the separation fluid, the distance between the injection member and the surface or the time the injection member resides in a certain position (or the speed at which the injection member is scanned over the surface). Manufacturing errors in the injection member will not cause corresponding errors in the width of cut, and moreover tubes which are commonly, and cheaply, available with high tolerance, e.g. stainless steel needles, can be used as the injection member.

It has been observed that alternative approaches which involve contact of a solid member with the selected path can have a significant risk of producing sub-bodies that are incompletely separated from each other. For example, it has been observed that in arrays of sub-bodies produced using the alternative approach a small subset of the sub-bodies are found to be connected together. Without wishing to be bound by theory, it is thought that these unwanted connections may result from proteins or other material attaching to the solid member while it is being moved along the selected path and disrupting the process of cutting of the first liquid into the sub-bodies by the solid member. This mechanism does not arise with the non-contact methods proposed herein and, indeed, unwanted incomplete separation of sub-bodies has not been observed using otherwise similar conditions.

It has also been observed that in alternative approaches which involve contact of a solid member with the selected path, debris can accumulate on the solid member while it is being used to cut the first liquid along the selected paths (e.g. vesicles or lumps of protein). This suggests that the cutting process removes materials from the first liquid and thereby undesirably modifies or disrupts the composition of the first liquid. Furthermore, the contact from the solid member can introduce defects or cuts along the selected path, which can also attract debris such as vesicles or lumps of protein. Such modifications or disruptions will be lower or negligible using the non-contact approach of the present disclosure.

In an embodiment, the distal tip is moved through both of the second liquid and the first liquid while propelling the separation fluid onto the selected path on the first substrate, for at least a portion of the selected path. In embodiments of this type, the movement of the distal tip assists with displacing the first liquid away from the volume adjacent to the selected path, thereby improving efficiency. In an embodiment, at least a portion of the distal tip of the injection member is configured to be more easily wetted by the second liquid than the first liquid. This facilitates efficient displacement of the first liquid by the second liquid by promoting efficient dragging of the second liquid through the first liquid in the wake of the distal tip. The dividing process can thereby be performed more reliably and/or at higher speed.

In an embodiment, the separation fluid comprises a portion of the second liquid; and the portion of the second liquid is propelled towards the selected path on the substrate by locally coupling energy into a region containing or adjacent to the portion of the second liquid to be propelled towards the selected path on the first substrate. The coupling of energy may comprise locally generating heat or pressure. This approach allows the dividing process to be formed quickly, flexibly and with high resolution. In some embodiments, the local coupling of energy is achieved using a focussed beam of electromagnetic radiation or ultrasound.

In an embodiment, for each of one or more of the sub-body footprints having a boundary that is all in contact with a closed loop of the selected path, the boundary comprises at least one straight line portion. Footprints with straight line portions allow higher space filling efficiency than the circular or elliptical footprints associated with alternative techniques based on depositing droplets. Forming sub-bodies by division rather than deposition greatly facilitates formation of such straight line portions. Square, rectangular, or other tessellating shapes may be formed for example.

In an embodiment, the second liquid is denser than the first liquid.

The method is surprisingly effective using a second liquid that is denser than the first liquid, despite the forces of buoyancy which might be expected to lift the first liquid away from contact with the substrate. Allowing use of a denser second liquid advantageously widens the range of compositions that can be used for the second liquid. Furthermore, the maximum depth of first liquid that can be retained stably in each sub-body without the first liquid spreading laterally over the substrate is increased.

In an embodiment, a material to be investigated is provided in the continuous body of the first liquid, and the division into sub-bodies generates a plurality of isolated samples that each contain a portion of the material to be investigated. In an embodiment, the material to be investigated comprises adherent living cells and at least a portion of the cells are allowed to adhere to the substrate before the continuous body of the first liquid is divided into the sub-bodies. A reagent (e.g. drug) is added to the continuous body of the first liquid after at least a portion of the adherent living cells have adhered to the substrate. The division into the sub-bodies is performed after the test substance has been added to the continuous body of the first liquid.

Thus, a methodology is provided which allows adhered living cells to be treated en masse after they have been allowed to adhere to a substrate and be divided into plural isolated samples later on. This is not possible using prior art approaches and saves considerable time and system complexity, particularly where it is desired to create large numbers of isolated samples and minimum disruption to the cells. It also ensures that cells in each sample have been exposed to very similar conditions, which is difficult to ensure when test substances (e.g. drugs) are added to individual wells or droplets manually, which may impose significant delays between treatment, and physical environments due to inkjet printing or the drop-seq method, of different samples. The cells can be placed on the surface without the stresses that would be imposed by passing them through a printing nozzle of an inkjet style printing system. Allowing the cells to adhere before dividing the first liquid provides a better representation of more classical well plate starting conditions for drug screening than alternative approaches in which cells are brought into miniature volumes before they adhere (e.g. via droplet printing). The inventors have furthermore found that cell survival is higher in the sub-bodies formed according to embodiments of the present disclosure in comparison to when the cells were added or present in droplets of the same volume prior to adhesion of the cells.

In an embodiment, the separation fluid comprises a liquid having the same composition as the second liquid; and the providing of the second liquid in direct contact with the continuous body of first liquid and covering the continuous body of first liquid comprises the following, after the continuous body of the first liquid in direct contact with the first substrate has been provided: propelling the separation fluid through the first liquid and into contact with the first substrate along at least a portion of the selected path while a portion of an upper interface of the first liquid is not yet in contact with the second liquid, the propelling of the separation fluid continuing until the separation fluid forms a layer of second liquid in direct contact with the continuous body of first liquid and covering the continuous body of first liquid.

Thus, for example, the process of propelling the separation fluid through the first liquid may start while the first liquid is exposed to air, without any second liquid yet being present. As the process proceeds, excess separation fluid rises above the first liquid and eventually covers the first liquid to thereby provide the layer of second liquid covering the first liquid. This approach is convenient because it removes the need for a user to provide the layer of second liquid as a step separate from the propelling of the separation fluid through the first liquid to form the sub-bodies. This saves time and simplifies the apparatus. Furthermore, the continuous body of the first liquid can be prepared (ready for the formation of the sub-bodies by the propelling of the separation fluid) well in advance without risk of disruption being caused by an overlaid layer of second liquid (because the layer of second liquid is not yet present). For example, prolonged overlay by the second liquid may cause variations in the depth of the first liquid prior to formation of the sub-bodies, which may lead to unwanted volume variations in the sub-bodies.

According to an alternative aspect, there is provided an apparatus for manufacturing a microfluidic arrangement, comprising: a substrate table configured to hold a substrate on which a continuous body of a first liquid is provided in direct contact with a substrate, and a second liquid is provided in direct contact with the first liquid and covering the first liquid; and a pattern forming unit configured to propel a separation fluid, immiscible with the first liquid, through at least the first liquid and into contact with the substrate along all of a selected path on the surface of the substrate, thereby displacing first liquid that was initially in contact with all of the selected path away from the selected path without any solid member contacting the selected path directly and without any solid member contacting the selected path via a globule of liquid held at a tip of the solid member, the selected path being such that the continuous body of the first liquid is divided to form a single sub-body of first liquid separated from the rest of the continuous body of first liquid by the second liquid or a plurality of sub-bodies of first liquid separated from each other by the second liquid, wherein: for each of one or more of the sub-bodies, a sub-body footprint represents an area of contact between the sub-body and the first substrate and all of a boundary of the sub-body footprint is in contact with a closed loop of the selected path surrounding the sub-body footprint.

Thus, an apparatus is provided that is capable of performing methods according to the disclosure.

Embodiments of the invention will now be described, by way of example only, with reference to the accompanying drawings in which corresponding reference symbols indicate corresponding parts, and in which.

Figure 22:
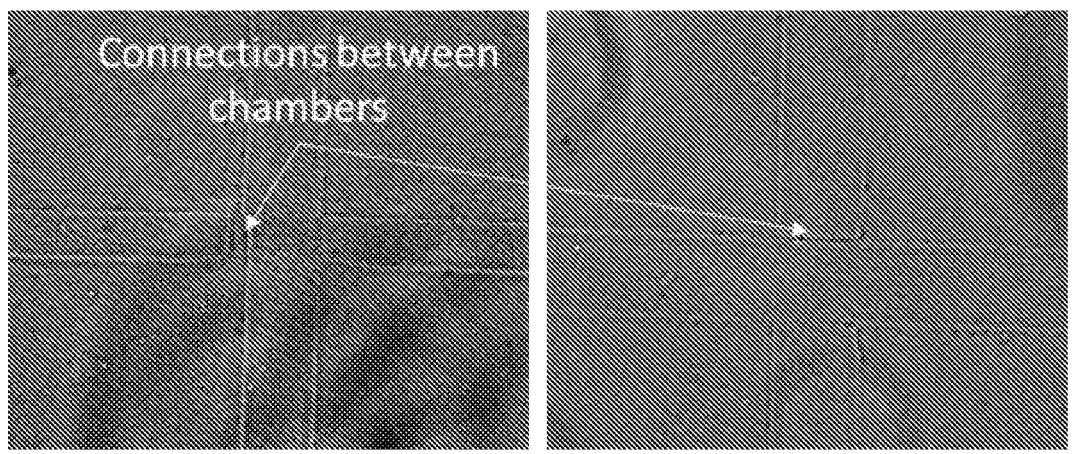
Figure 23:
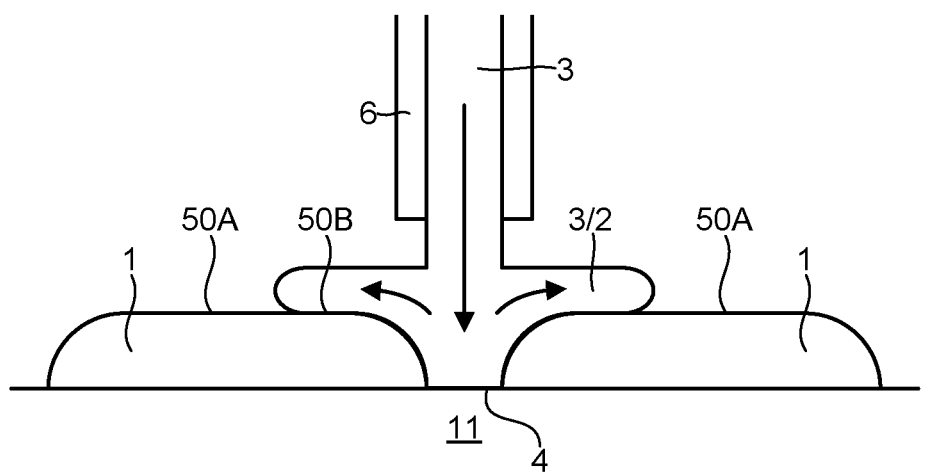
Figure 24:
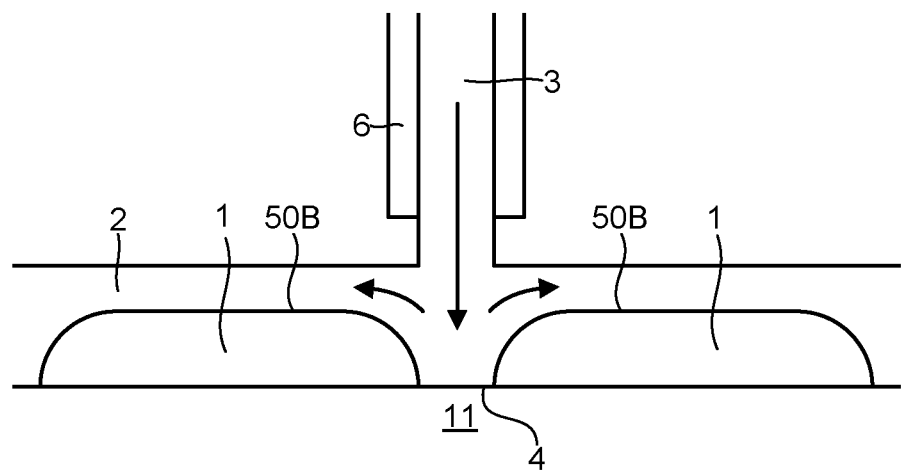

FIG. 22 depicts images of unwanted connections between sub-bodies of liquid that can occur using alternative techniques; and FIGS. 23 and 24 are schematic side sectional views showing steps in a method of manufacturing a microfluidic arrangement in which a separation fluid is propelled initially through a continuous body of first liquid that is not covered by any second liquid; FIG. 23 depicts an initial stage in which the separation fluid is only just starting to cover the first liquid, such that a portion of an upper interface of the first liquid is not yet in contact with any second liquid; FIG. 24 depicts a later stage in which the separation fluid, which may now be referred to as the second liquid, completed covers the first liquid.

The figures are provided for explanatory purposes only and are not depicted to scale in order to allow constituent elements to be visualised clearly. In particular, the width of the receptacle providing the first substrate relative to the depth of the first and second liquids will typically be much larger than depicted in the drawings.

Methods are provided for conveniently and flexibly manufacturing a microfluidic arrangement.

Figure 1:
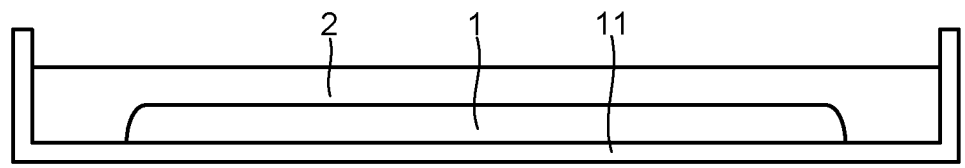
FIG. 1 is a schematic side view of a continuous body of a first liquid on a substrate with a second liquid in direct contact with the first liquid and covering the first liquid.

As depicted schematically in FIG. 1, a continuous body of a first liquid 1 is provided. The first liquid 1 is in direct contact with a first substrate 11. In an embodiment the first liquid 1 comprises an aqueous solution but other compositions are possible. A second liquid 2 is provided in direct contact with the first liquid 1. The second liquid 2 is immiscible with the first liquid. In an embodiment, the continuous body of the first liquid 1 is formed on the first substrate 11 before the second liquid 2 is brought into contact with the first liquid 1. In other embodiments, the continuous body of the first liquid 1 is formed after the second liquid 2 is provided (e.g. by injecting the first liquid 1 through the first liquid 2). In embodiments in which the microfluidic arrangement is to be used for testing samples of biological material, the continuous body of the first liquid 1 will normally be formed before the second liquid 2 is provided. The second liquid 2 covers the first liquid 1. The first liquid 1 is thus completely surrounded and in direct contact exclusively with a combination of the second liquid 2 and the first substrate 11. At this point in the method the first liquid 1 is not in contact with anything other than the second liquid 2 and the first substrate. Typically, the first substrate 11 will be unpatterned (neither mechanically nor chemically), at least in the region in contact with (typically underneath) the continuous body of the first liquid 1. In an embodiment, the continuous body of the first liquid 1 is in direct contact exclusively with a substantially planar portion of the first substrate 11 and the second liquid 2.

Figure 2:
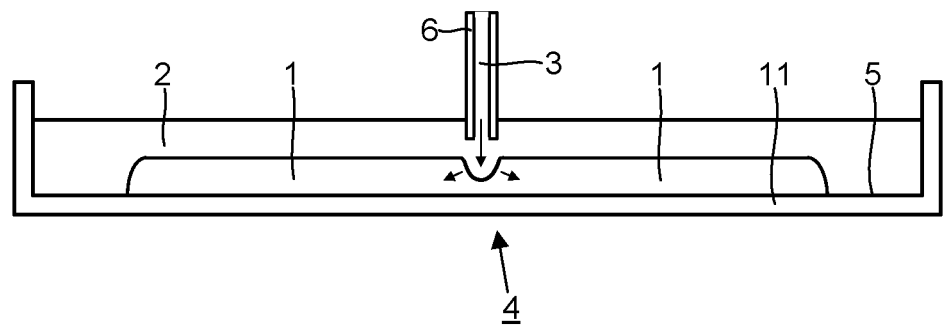
FIG. 2 is a schematic side view of the arrangement of FIG. 1 during dividing of the continuous body of the first liquid by pumping a separation fluid out of a distal tip of an injection member.

In a subsequent step, an example implementation of which is depicted in FIG. 2, a separation fluid 3 is propelled through at least the first liquid 1 (and optionally also through a portion of the second liquid 2, as shown in the example of FIG. 2) and into contact with the first substrate 11 along all of a selected path 4 on the surface 5 of the first substrate 11. The selected path 4 consists of a portion of the surface area of the surface 5 of the first substrate 11. The selected path 4 thus has a finite width. Portions of the selected path may be substantially elongate and interconnected, the selected path thereby forming a network or web-like pattern. The separation fluid 3 is immiscible with the first liquid 1. The separation fluid 3 displaces the first liquid 1 away from the selected path 4 without any solid member contacting the selected path directly (e.g. by dragging a tip of the solid member over the surface of the first liquid) and without any solid member contacting the selected path via a globule of liquid held at a tip of the solid member (e.g. by dragging the globule of liquid, held stationary relative to the tip, over the surface). The first liquid 1 is initially in contact with all of the selected path 4. The surface area defined by the selected path 4 therefore represents a portion of the surface area of the first substrate 11 in which the first liquid 1 has been displaced away from contact with the first substrate 11 by the separation fluid 3 that has been propelled through the first liquid 1. In the embodiment of FIG. 2, the separation fluid 3 is propelled onto the selected path 4 from a lumen in a distal tip 6 of an injection member while the distal tip 6 is scanned over the first substrate 11. No contact is therefore made in this embodiment between the distal tip 6 and the selected path 4 during at least a portion of the selected path 4. No contact is made by the selected path with any other solid member, either directly or via a globule of liquid that is stationary relative to the solid member, for at least a portion of the selected path 4. The momentum of the separation fluid 3 is sufficient to force the first liquid 1 to be displaced away from the selected path 4. In an embodiment, the separation fluid 3 is pumped continuously out of the distal tip for at least a portion of the selected path. In the embodiment shown in FIG. 2, the separation fluid 3 is pumped out of the distal tip 6 in a direction that is substantially perpendicularly to the selected path at the location of the distal tip 6. In other embodiments, the distal tip 6 may be tilted so as to pump the separation fluid 3 towards the selected path 4 at an oblique angle relative to the selected path 4.

Figure 3:
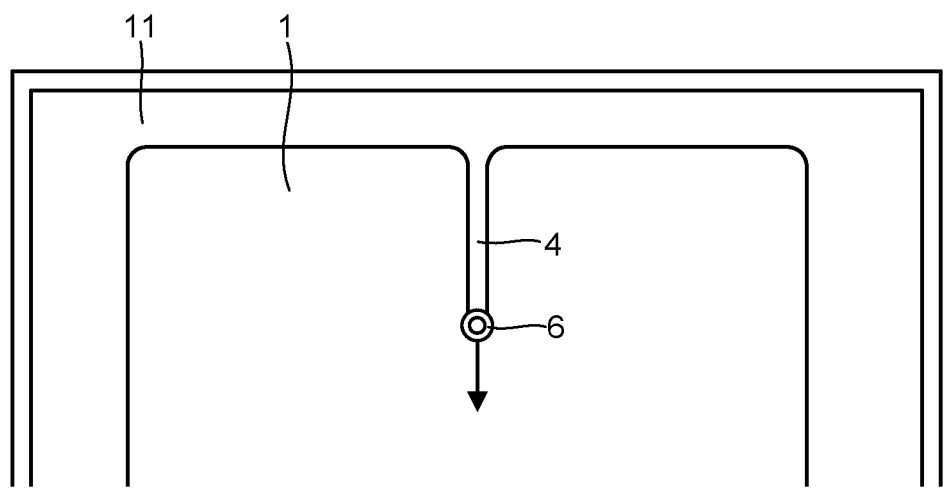
FIG. 3 is a schematic top view of the arrangement of FIG. 2.
Figure 4:
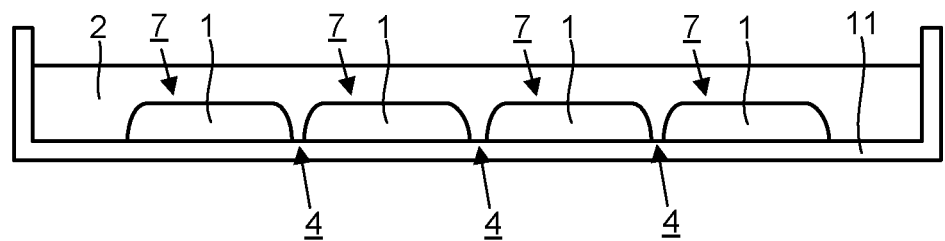
FIG. 4 is a schematic side view showing a subsequent step of further dividing a sub-body.
Figure 5:
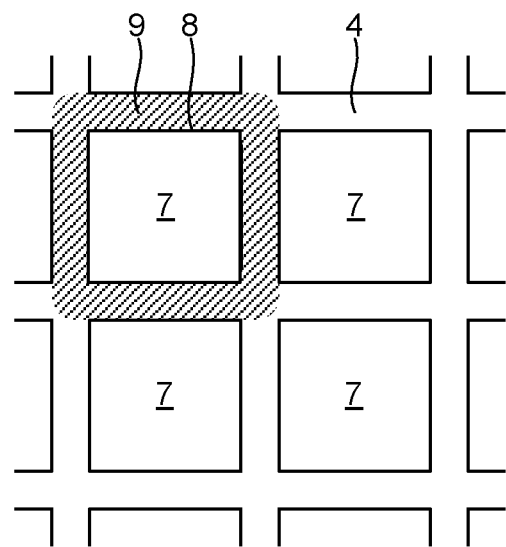
FIG. 5 is a schematic top view of a portion of microfluidic arrangement formed using the steps of FIGS. 2-4 showing a closed loop of the selected path surrounding and in contact with a boundary of a sub-body.

As depicted for example in FIGS. 3-5, the selected path 4 is such that the continuous body of the first liquid 1 is divided into a plurality of sub-bodies 7 of the first liquid 1. Each sub-body 7 is separated from each other sub-body 7 by the second liquid 2. Thus, when the first liquid 1 is displaced away from the selected path 4 by the propelled separation fluid 3, the second liquid 2 moves into contact with the selected path 4 and remains stably in contact with the selected path 4. A pinning line (associated with interfacial forces) stably holds the plurality of sub-bodies 7 of the first liquid 1 separated from each other by the second liquid 2. The plurality of sub-bodies 7 may comprise a single useful sub-body 7 and a remainder of the continuous body of the first liquid 1 (which may be considered as another sub-body) or may comprise plural useful sub-bodies (e.g. plural reservoirs for receiving reagents etc.), optionally together with any remainder of the continuous body of the first liquid 1.

The method allows sub-bodies 7 of the first liquid 1 to be formed flexibly on the first substrate 11 without any mechanical or chemical structures being created beforehand to define the geometry of the sub-bodies 7.

The particular compositions of the first liquid 1, second liquid 2, the separation fluid and first substrate 11 are not particularly limited. However, it is desirable that the first liquid 1 and the second liquid 2 can wet the first substrate 11 sufficiently for the method to operate efficiently. Furthermore, it is desirable that no phase change occurs during the manufacturing of the microfluidic arrangement. For example, the separation fluid, first liquid 1 and second liquid 2 may all be liquid before the microfluidic arrangement is formed and remain liquid during the manufacturing process and for a prolonged period after the microfluidic arrangement is formed and during normal use of the microfluidic arrangement. In an embodiment, the first liquid 1, second liquid 2 and first substrate 11 are selected such that an equilibrium contact angle of a droplet of the first liquid 1 on the first substrate 11 in air and an equilibrium contact angle of a droplet of the second liquid 2 on the first substrate 11 in air would both be less than 90 degrees. In an embodiment, the first liquid 1 comprises an aqueous solution. In this case the first substrate 11 could be described as hydrophilic. In an embodiment, the second liquid 2 comprises a fluorocarbon such as FC40 (described in further detail below). In this case the first substrate 11 could be described as fluorophilic. In the case where the first liquid 1 is an aqueous solution and the second liquid 2 is a fluorocarbon, the first substrate 11 could therefore be described as being both hydrophilic and fluorophilic.

The separation fluid 3 may comprise one or more of the following: a gas, a liquid, a liquid having the same composition as the second liquid 2, a portion of the second liquid 2 provided before the propulsion of the separation fluid 3 through the first liquid 1.

In some embodiments, as mentioned above, the separation fluid 3 is propelled onto the selected path 4 on the first substrate 11 from a lumen (e.g. by continuously pumping the separation fluid 3 out of the lumen, optionally at a substantially constant rate) in a distal tip 6 of an injection member while the distal tip 6 is moved relative to (e.g. scanned over or under along a path corresponding to the selected path 4) the first substrate 11 (with some first liquid 1 and, optionally, second liquid 2, between the distal tip 6 and the first substrate 11). In some embodiments of this type, the distal tip 6 is moved through both of the second liquid 2 and the first liquid 1 while propelling the separation fluid 3 onto the selected path 4 on the first substrate 11, for at least a portion of the selected path 4. The distal tip 6 is thus held relatively close to the first substrate 11. In such embodiments, the movement of the distal tip 6 and the flow of the separation fluid 3 towards the first substrate 11 both act to displace the first liquid 1 away from the first substrate 11, allowing the second liquid 2 to move into the volume previously occupied by the first liquid 1. In an embodiment, this process is facilitated by arranging for at least a portion of the distal tip 6 to be more easily wetted by the second liquid 2 than by the first liquid 1. In this way, it is energetically more favourable for the second liquid 2 to flow into the region behind the moving distal tip 6 and thereby displace the first liquid 1 efficiently. Preferably the first substrate 11 is also configured so that it is more easily wetted by the second liquid 2 than by the first liquid 1, thereby energetically favouring contact between the second liquid 2 and the first substrate 11 along the selected path 4. This helps to maintain a stable arrangement in which the sub-bodies 7 are separated from each other by second liquid in contact with the selected path 4. In other embodiments, an example of which is shown in FIG. 2, the distal tip 6 is moved through the second liquid 2 but not the first liquid 1 while propelling the separation fluid 3 onto the selected path 4 on the first substrate 11, for at least a portion of the selected path 4. The distal tip 6 is thus held further away from the first substrate 11. This approach helps to avoid detachment of droplets of the first liquid 1 from the first substrate 11 caused by the pumping of the separation fluid 3 against the first substrate 11.

FIGS. 2-5 illustrate an example embodiment. FIGS. 2 and 3 depicts movement of a distal tip 6 through the second liquid 2 but not the first liquid 1 in a horizontal direction, parallel to a plane of the first substrate 11 in contact with (typically underneath) the first liquid 1. Separation fluid 3 is pumped from the distal tip 6. The vertical arrow exiting the distal tip 6 in FIG. 2 schematically represents a pumped flow of the separation fluid 3. Arrows within the first liquid 1 in FIG. 2 schematically represent movement of the first liquid 1 away from the region above a portion of the selected path 4, which will eventually allow the second liquid 2 to contact the first substrate 11 along the selected path 4. In FIG. 2, the movement of the distal tip 6 is into the page. In FIG. 3, the movement is downwards. In an embodiment, the distal tip 6 is maintained at a constant distance from the first substrate 11 while the distal tip 6 is being moved through the second liquid 2. When completed, the process of FIGS. 2 and 3 will result in the continuous body of the first liquid 1 of FIG. 1 being divided into two sub-bodies. The process can be repeated and/or performed in parallel to create the desired number and size of individual sub-bodies 7. The pumping of the separation fluid 3 is optionally stopped and started between movement of the distal tip 6 over different portions of the selected path, or the pumping may continue as the distal tip moves from the end of one portion of the selected path to the start of the next portion of the selected path. FIG. 4 depicts the result of repeating the steps of FIGS. 2 and 3 to create three parallel lines of a selected path 4 (with the pumping of the separation fluid 3 being optionally stopped and started between formation of each of the three parallel lines, or the pumping may continue while the distal tip moves from the end of one parallel line to the start of the next parallel line). By repeating the process in the orthogonal direction 16 square sub-bodies 7 could be provided. In practice, many 100s or 1000s of sub-bodies 7 could be provided in this manner. The inventors have demonstrated for example that the approach can be used routinely to obtain a square array of sub-bodies having a pitch of less than 100 microns. This is considerably smaller than would be possible using standard microwell plate manufacturing techniques.

As depicted for one of the sub-bodies 7 in FIG. 5, the selected path 4 is such that, for each of one or more of the sub-bodies 7, a sub-body footprint represents an area of contact between the sub-body 7 and the first substrate 11 and all of a boundary 8 of the sub-body footprint is in contact with a closed loop 9 of the selected path 4 (an example of which is depicted by hatching in FIG. 5) surrounding the sub-body footprint. The closed loop 9 of the selected path 4 is defined as any region that represents a portion of the surface area of the first substrate 11 that forms part of the selected path 4, that forms a closed loop, and that is in contact with the boundary 8 of sub-body 7 along all of the boundary 8 of the sub-body 7. The first liquid 1, second liquid 2 and first substrate 11 are configured (e.g. by selecting their compositions) such that each boundary 8 of a sub-body footprint that is all in contact with a closed loop 9 of the selected path 4 is pinned in a static configuration by interfacial forces, with the first liquid 1 and second liquid 2 remaining in liquid form. Thus, interfacial forces, which may also be referred to as surface tension, establish pinning lines that cause the sub-body footprints to maintain their shape. The stability of the sub-bodies 7 formed in this way is such that liquid can be added to or removed from each sub-body 7, within limits defined by the advancing and receding contact angles along the boundary 8, without changing the sub-body footprint. In some embodiments the boundary 8 of the sub-body footprint that is all in contact with the closed loop 9 of the selected path 4 is made continuously (i.e. in a single process without interruption), and in the embodiment illustrated in FIG. 5 it is made in four separate steps.

In some embodiments, the separation fluid 3 comprises a portion of the second liquid 2 and the portion of the second liquid 2 is propelled towards the selected path 4 by locally coupling energy into a region containing or adjacent to the portion of the second liquid 2 to be propelled towards the selected path 4 on the first substrate 11. The energy coupling may comprise locally generating heat or pressure. The energy may cause expansion, deformation, break-down, ablation or cavitation of material that results in a pressure wave being transmitted towards the portion of the second liquid 2 to be propelled. In some embodiments, the coupling of energy is implemented using a focussed beam of a wave such as electromagnetic radiation or ultrasound. The coupling of energy may occur at or near a focus of the beam.

In an embodiment, a focus of the beam is scanned along a scanning path based on (e.g. following) the geometry of the selected path 4. When viewed perpendicularly to a surface of the first substrate 11 on which the selected path 4 is formed, the scanning path may overlap with at least a portion of the selected path 4 and/or run parallel to at least a portion of the selected path. All or a majority of the scanning path may be below, above or at the same level as the selected path 4 (and, therefore, the surface of the first substrate 11).

In some embodiments, energy from the beam absorbed in the first substrate 11 causes the first liquid 1 to be locally forced away from the first substrate 11 along the selected path 4, the second liquid 2 moving into contact with the first substrate 11 where the first liquid 1 has been forced away (i.e. along the selected path 4). The absorption of the beam in the first substrate 11 may cause local deformation or ablation of the first substrate 11, the localized deformation or ablation transmitting a corresponding localized thrust to first liquid 1 initially in contact with a respective portion of the selected path on the first substrate 11. Using a laser to apply localized thrust to liquids is described in the context of forward printing (i.e. where matter is transferred onto an initially unpatterned substrate to provide a pattern) in, for example, A. Piqué et al. "Direct writing of electronic and sensor materials using a laser transfer technique," J. Mater. Res. 15(9), 1872-1875 (2000). Methods using this approach have been referred to as laser-induced forward transfer (LIFT) methods. The inventors have recognised that these techniques could be adapted to divide a continuous body of a first liquid 1 into sub-bodies 7 as described herein.

Figure 6:
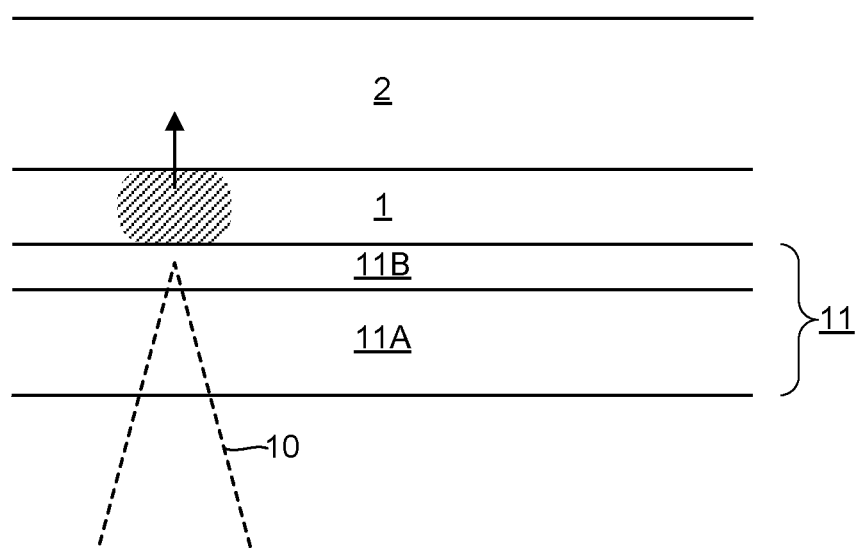
FIG. 6 is a schematic side sectional view showing focusing of a laser beam into an intermediate absorbing layer of a substrate to propel first liquid away from the substrate and thereby allow the second liquid to move into contact with a selected path on the substrate.

An example of such a configuration is depicted schematically in FIG. 6. In this example, the first substrate 11 comprises a first base layer 11A and a first intermediate absorbing layer 11B between the first base layer 11A and the first liquid 1. A beam absorbance per unit thickness of the first intermediate absorbing layer 11B is higher than a beam absorbance per unit thickness of the first base layer 11A. Energy from the beam absorbed in the first intermediate absorbing layer 11B causes the first liquid 1 to be locally forced away from the first substrate 11 along the selected path 4. A portion of the first liquid 1 to be locally forced away is schematically indicated by hatching in FIG. 6. The second liquid 2 moves into contact with the first substrate 11 where the first liquid 1 has been forced away. The provision of an intermediate absorbing layer 11B that is more absorbing than the base layer 11A provides greater flexibility for choosing a composition of the first substrate 11. For example, the first substrate 11 can be formed predominantly from a material that is relatively transparent to the beam but optimized for other properties, while the first intermediate absorbing layer 11B, which can be provided as a thin film, can be configured specifically to provide a level of absorption and/or other properties that promote efficient localized forcing of the first liquid 1 away from the first substrate 11. In an embodiment, as depicted in FIG. 6, the beam is focused within the first substrate 11 and optionally, where provided, within the first intermediate absorbing layer 11B, to maximise absorption in the first substrate 11 and/or allow the overall beam intensity to be kept as low as possible while still imparting sufficient localized thrust to the first liquid 1. Minimizing the overall beam intensity may be particularly desirable when the first liquid 1 comprises material, such as biological material, that may be adversely affected by the beam. In the example of FIG. 6, the beam 10 is applied from a side of the first substrate 11 opposite to the first liquid 1 and second liquid 2 (i.e. from below in the orientation of FIG. 6). In other embodiments, the beam 10 may be applied from the other side of the first substrate 11, thereby traversing the second liquid 2 before interacting with the first substrate 11.

Figure 7:
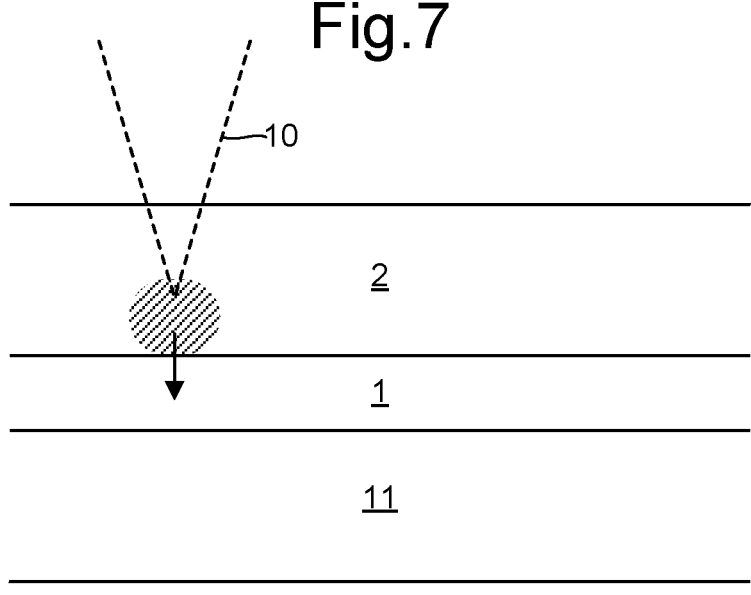
FIG. 7 is a schematic side sectional view showing focusing of a laser beam into the second liquid to propel a portion of the second liquid through the first liquid and onto a selected path on the substrate.

FIG. 7 depicts an example of an alternative embodiment in which a focus of the beam 10 is positioned within the second liquid 2 while the portion of the second liquid 2 is propelled towards the selected path 4 on the first substrate 11. In some embodiments of this type, the beam causes cavitation in a localized region of the second liquid 2. The cavitation occurs when the absorption in the second liquid 2 is high enough to overcome the optical breakdown threshold of the second liquid 2, which results in generation of a plasma that induces formation of a cavitation bubble. The beam should ideally be tightly focussed with very short laser pulses (e.g. sub-picosecond laser pulses). The cavitation bubble expands and applies a thrust to second liquid 2 in neighbouring regions. If the focus of the beam is positioned adjacent to a portion of the selected path 4, the thrust applied to the neighbouring regions of the second liquid 2 can propel a portion of the second liquid 2 (depicted schematically by hatching in FIG. 7) through the first liquid 1 and into contact with the selected path 4. A diode pumped Yb:KYW femtosecond laser (1027 nm wavelength, 450 fs pulse duration, 1 kHz maximum repetition rate) having a beam waist of around 1.2 microns could be used, for example, as per M. Duocastella et al., "Film-free laser forward printing of transparent and weakly absorbing liquids" OPTICS EXPRESS 11 Oct. 2010/Vol. 18, No. 21 pages 21815-21825, which describes propulsion of droplets via laser induced cavitation within a liquid for the purpose of forward printing droplets from a body of liquid onto a substrate facing the body of liquid. It will be understood that various deviations from the exact laser specifications above could be applied without departing from the underlying principle of operation.

Figure 8:
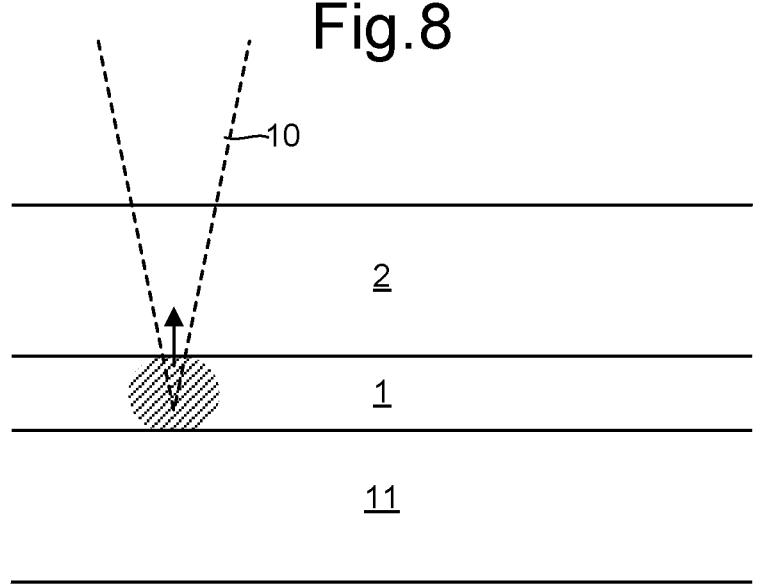
FIG. 8 is a schematic side sectional view showing focusing of a laser beam into the first liquid to propel first liquid away from the substrate and thereby allow the second liquid to move into contact with a selected path on the substrate.

FIG. 8 depicts a variation of the approach depicted in FIG. 7 in which the beam 10 propels the second liquid 2 by causing cavitation in the first liquid 1, the cavitation causing the first liquid 1 to be locally forced away from the first substrate 11, the second liquid 2 moving into contact with the first substrate 11 where the first liquid 1 has been forced away. This may be achieved for example by focussing the beam within the first liquid 1. The portion of the first liquid 1 propelled away from the first substrate 11 by cavitation is depicted schematically by hatching in FIG. 8.

Figure 9:
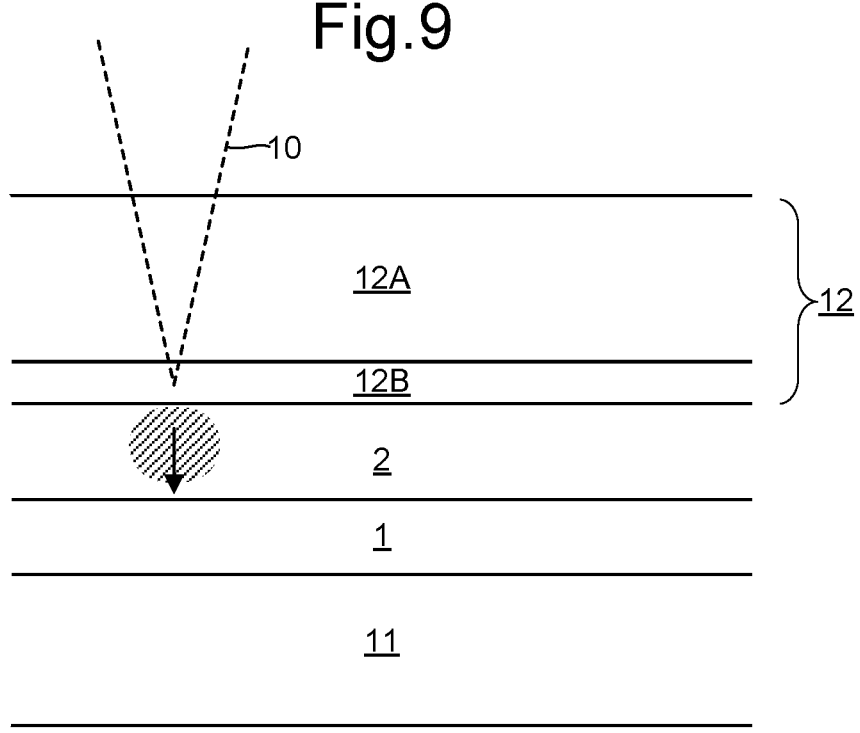
FIG. 9 is a schematic side sectional view showing focusing of a laser beam into an intermediate absorbing layer of a second substrate to propel a portion of the second liquid through the first liquid and onto a selected path on the substrate.

FIG. 9 depicts an example of an alternative embodiment in which a second substrate 12 is provided. The second substrate 12 faces at least a portion of the first substrate 11 and is in contact with liquid. There is a continuous liquid path between the second substrate 12 and the first substrate 11. In the example shown, the second substrate 12 is in contact with the second liquid 2. In this embodiment, energy from the beam 10 is absorbed in either or both of the second substrate 12 and liquid adjacent to the second substrate 12 and causes the second liquid 2 to be locally forced away from the second substrate 12, thereby providing the propulsion of the second liquid 2 towards the selected path 4 on the first substrate 11. In the example shown, the second substrate 12 comprises a second base layer 12A and a second intermediate absorbing layer 12B between the second base layer 12A and the second liquid 2. A beam absorbance per unit thickness of the second intermediate absorbing layer 12B is higher than that of the second base layer 12A. Energy from the beam absorbed in the second intermediate absorbing layer 12B causes the second liquid 2 to be locally forced away from the second substrate 12, thereby providing the propulsion of the second liquid 2 towards the selected path on the first substrate 11. In an embodiment, as depicted in FIG. 9, the beam 10 is focused within the second substrate 12 and optionally, where provided, within the second intermediate absorbing layer 12B, to maximise absorption in the second substrate 12 and/or allow the overall beam intensity to be kept as low as possible while still imparting sufficient localized thrust to the second liquid 2.

In an embodiment, the second substrate 12 floats on liquid (e.g. the second liquid 2) in contact with the second substrate 12. This approach allows the second substrate 12 to be levelled easily and reliably, thereby facilitating accurate alignment of a focus position within the second substrate 12 (e.g. within a second intermediate absorbing layer 12B).

Figure 10:
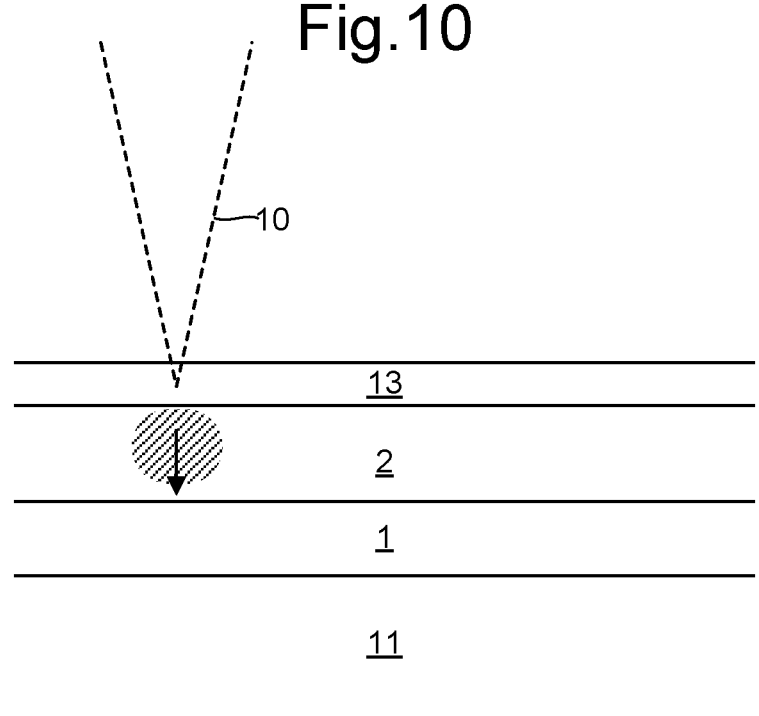
FIG. 10 is a schematic side sectional view showing focusing of a laser beam into a third liquid to propel a portion of the second liquid through the first liquid and onto a selected path on the substrate.

FIG. 10 depicts a variation on the embodiment discussed above with reference to FIG. 9 in which a layer of third liquid 13 is provided above the second liquid 2. A beam absorbance per unit thickness of the third liquid 13 is higher than a beam absorbance per unit thickness of the second liquid 2. Energy from the beam 10 absorbed in the third liquid 13 causes the second liquid 2 to be locally propelled towards the selected path 4 on the first substrate 11. Using a third liquid 13 having higher absorbance than the second liquid 2 provides greater flexibility for choosing the composition of the second liquid 2. The second liquid 2 can be optimized to provide stable separation of the sub-bodies 7, for example, without being restricted by the need to provide sufficient absorbance to allow the beam to cause cavitation in the second liquid 2 for propelling the second liquid 2 through the first liquid 1. The third liquid 13 can be optimized for absorbing the beam and initiating the formation of a cavitation bubble for locally propelling the second liquid 2 towards the first substrate 11.

Figure 11:
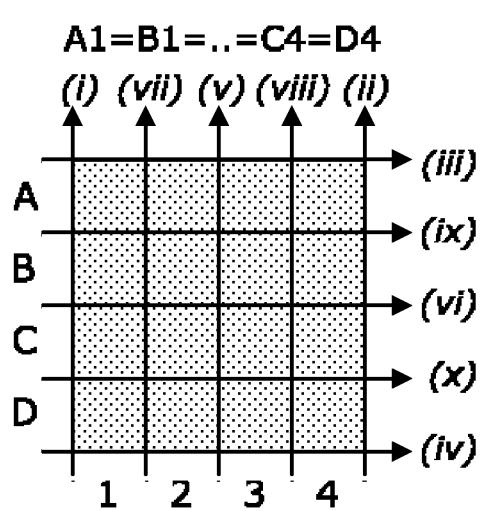
FIG. 11 depicts a dividing scheme resulting in sub-bodies of equal volume.

In an embodiment, a sequence of the dividing process is selected to control the relative volumes of the sub-bodies 7 formed. In an embodiment, as depicted in FIG. 11, the dividing of the continuous body of the first liquid 1 into sub-bodies 7 comprises the following steps in order: dividing the continuous body of the first liquid 1 symmetrically into two sub-bodies of equal volume; and repeatedly dividing each sub-body formed by a preceding dividing step symmetrically into two further sub-bodies of equal volume. The symmetrical division may comprise division along a line of mirror symmetry of the body or sub-body being divided. FIG. 11 depicts an example sequence. The roman numerals depict the order of a sequence of straight line trajectories of a distal tip 6 of an injection member over the selected path 4 (in this case, straight lines). The trajectories (i)-(iv) first isolate a square initial continuous body of the first liquid 1. Subsequent trajectories (v)-(x) then progressively divide the continuous body and sub-bodies formed therefrom symmetrically into equal volumes until an array of 16 sub-bodies is provided. The symmetrical division at each stage ensures that each and every sub-body has the same volume (thus, the volume of A1=B1= . . . C4=D4). An array of any number may be created.

Figure 12:
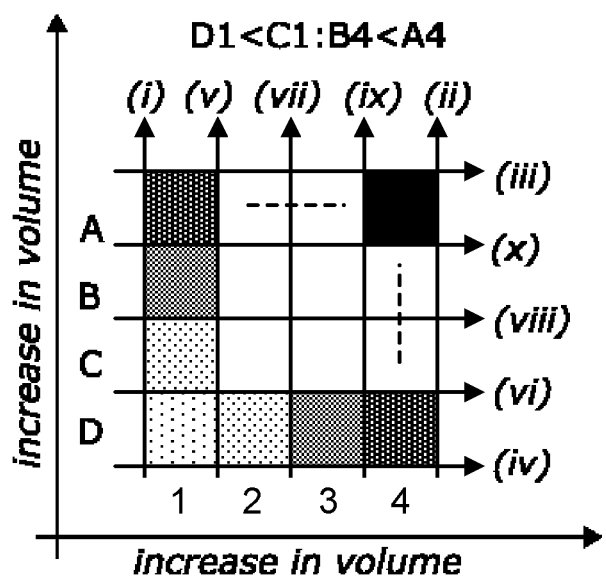
FIG. 12 depicts a dividing scheme for controllably providing sub-bodies of different volumes.

FIG. 12 depicts an alternative dividing scheme for controllably providing sub-bodies of progressively increasing volumes. In this case, trajectories (i)-(iv) are again provided for isolating a square initial continuous body of the first liquid 1. The subsequent trajectories (v)-(x) then scan progressively from the lower left corner to the upper right corner, in each case cutting the continuous body or sub-bodies formed therefrom asymmetrically (except for the final two cuts). The result of this process is that the first liquid is gradually pushed upwards and to the right, leading to a progressive increase in the relative volumes of the sub-bodies (i.e. a progressive increase in their depths) upwards and to the right. This occurs due to a net movement of the first liquid away from the cutting line due to the formation of a curved edge (non-uninform depth) of first liquid 1 along the cutting line. Thus, for each cut there will be a net movement of liquid into the larger of the two sub-bodies formed by the cut.

In an embodiment, for each of one or more of the sub-body footprints having a boundary 8 that is all in contact with a closed loop of the selected path 4, the boundary 8 comprises at least one straight line portion. This can be achieved for example by forming the sub-bodies 7 using straight line cuts such as those described above with reference to FIGS. 2-5. The array of sub-bodies 7 formed in this manner is therefore fundamentally different to alternative techniques involving deposition of droplets onto the surface of a substrate (where the droplets would have a curved outline). A higher level of space filling is therefore made possible. In an embodiment, at least a subset of the sub-body footprint outlines tessellate with respect to each other. For example, the sub-body footprints may comprise squares, rectangles or parallelograms. All these four-sided shapes can be formed efficiently by performing straight line cuts such as those discussed above with reference to FIGS. 2-5.

In an embodiment, the second liquid 2 is denser than the first liquid 1. The inventors have found that despite the buoyancy forces imposed on the first liquid 1 by the denser second liquid 2 above the first liquid 1, the first liquid 1 surprisingly remains stably in contact with the first substrate 11 due to surface tension effects (interfacial energies) between the first liquid 1 and the first substrate 11. Allowing use of a denser second liquid 2 is advantageous because it widens the range of compositions that are possible for the second liquid 2. For example, in a case where the first liquid 1 is an aqueous solution, a fluorocarbon such as FC40 can be used, which provides a high enough permeability to allow exchange of vital gases between cells in the sub-bodies 7 and the surrounding atmosphere through the layer of the second liquid 2. FC40 is a transparent fully fluorinated liquid of density 1.8555 g/ml that is widely used in droplet based microfluidics. Using a second liquid 2 that is denser than the first liquid 1 is also advantageous because it increases the maximum depth of first liquid 1 that can be retained stably in each sub-body 7 without the first liquid 1 spreading laterally over the first substrate 11. This is because the weight of the first liquid 1 would tend to force the sub-body 7 downwards and therefore outwards and this effect is counteracted by buoyancy. The second liquid 2 may also advantageously increase the contact angle compared to air.

Figure 13:
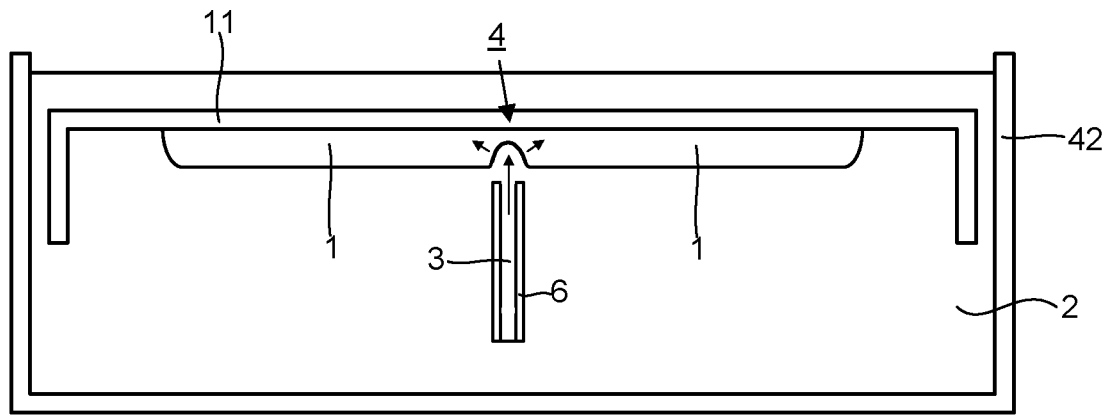
FIG. 13 depicts dividing of a continuous body of the first liquid while the continuous body is held upside down.

In the embodiments discussed above the microfluidic arrangement is formed on an upper surface of a first substrate 11. In other embodiments, as depicted in FIG. 13, the microfluidic arrangement can be formed on a lower surface of the first substrate 11. The dividing of the continuous body of the first liquid 1 can thus be performed with the first substrate 11 inverted relative to the arrangement of FIG. 2. In this case, surface tension can hold the first liquid 1 in contact with the first substrate 11. The first substrate 11 and first liquid 1 can then be immersed in a bath 42 containing the second liquid 2 while the continuous body of the first liquid 1 is divided into sub-bodies. The subsequent steps described above with reference to FIGS. 2-5 could be performed starting from the arrangement of FIG. 13. This approach may be convenient where the microfluidic arrangement is to be used for the formation of 3D cell culture spheroids for example.

In an embodiment, the continuous body of the first liquid 1 is laterally constrained predominantly by surface tension. For example, the continuous body of the first liquid 1 may be provided only in a selected region on the first substrate 11 rather than extending all the way to a lateral wall (e.g. where the first substrate 11 is the bottom surface of a receptacle comprising lateral walls, as depicted in FIG. 1). The continuous body is thus not laterally constrained by a lateral wall. This arrangement is particularly desirable where the second liquid 2 is denser than the first liquid 1 because it provides greater resistance against disruptions to the uniformity of thickness of the continuous body of the first liquid 1 due to downward forces on the first liquid 1 from the second liquid 2. The inventors have found that the depth of the first liquid 1 can as a consequence be higher when the first liquid 1 is laterally constrained predominantly by surface tension than when this is not the case. Providing an increased depth of the first liquid 1 is desirable because it allows larger sub-body volumes for a given spatial density of sub-bodies on the first substrate 11. When the sub-bodies 7 are used for culturing cells, for example, the cells may therefore be provided with higher amounts of the required materials, allowing the cells to survive longer and/or under more uniform conditions before further action needs to be taken.

In other embodiments, the continuous body of the first liquid 1 may be allowed to extend to the lateral walls of a receptacle providing the first substrate 11. A thin film of the first liquid 1 may conveniently be formed in this way by providing a relatively deep layer of the first liquid 1 filling the bottom of the receptacle and then removing (e.g. by pipetting) the first liquid 1 to leave a thin film of the first liquid 1.

Figure 14:
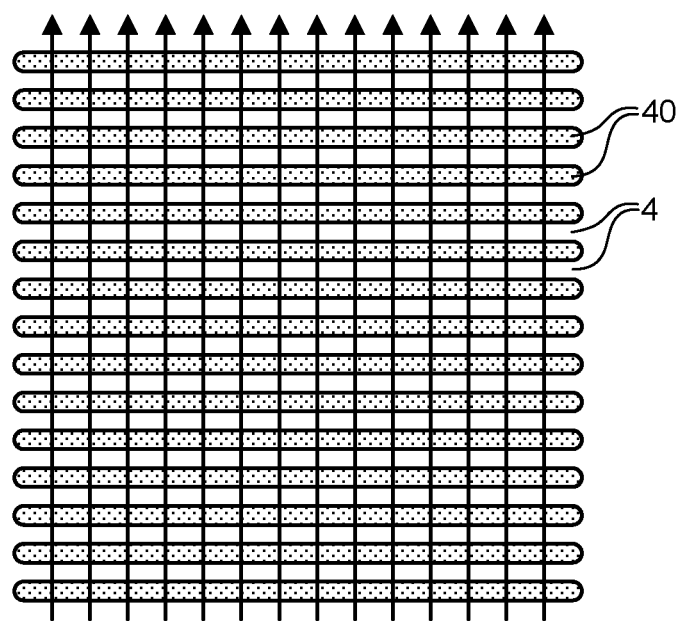
FIG. 14 depicts a dividing scheme in which a continuous body of the first liquid is divided into parallel elongate strips in a first step, wherein each strip is subsequently divided into a plurality of sub-bodies.

In an embodiment, the continuous body of the first liquid 1 is divided into a plurality of elongate strips 40 (the first liquid 1 in each strip 40 being depicted by hatching for clarity) in an initial step of dividing the continuous body of the first liquid 1 into sub-bodies. In an embodiment, the elongate strips 40 are parallel to each other. An example of such an arrangement is depicted in FIG. 14. The arrangement could be formed for example by propelling the separation fluid 3 into contact with the selected path 4 along a series of parallel horizontal trajectories. In a subsequent step, a substance is added to one or more localized regions (e.g. lateral ends) of one or more of the elongate strips 40. The substance migrates (e.g. by diffusion and/or advection) along each elongate strip 40, thereby creating a concentration gradient along the elongate strip 40. In a subsequent step the elongate strips are divided into a plurality of sub-bodies, thereby quickly and easily creating sets of sub-bodies having different concentrations of a selected substance within them. In the particular example of FIG. 14, the division of the elongate strips 40 into the plurality of sub-bodies is performed by moving a distal tip 6 of an injection member along the trajectories marked by solid line arrows in FIG. 14 while continuously ejecting the separation fluid 3 from the distal tip 6.

Figure 15:
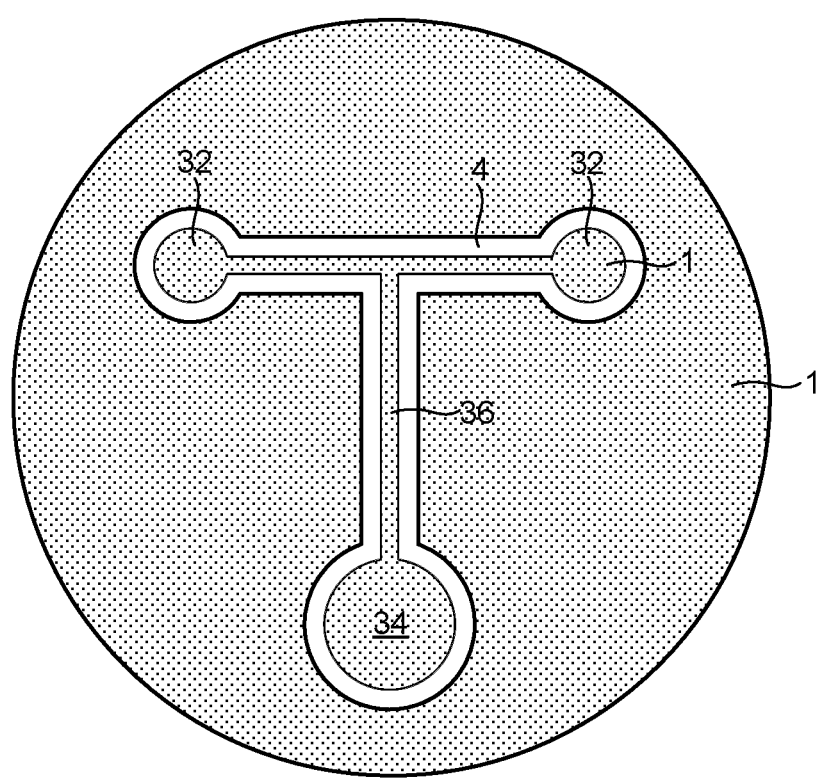
FIG. 15 depicts a dividing scheme in which a continuous body of the first liquid is divided to form at least one sub-body comprising a conduit connected to at least one reservoir.

In an embodiment, more complex shapes can be formed by the dividing of the continuous body of the first liquid 1 into sub-bodies. In one example, as depicted in FIG. 15 in which regions of the first liquid 1 are hatched for clarity, the continuous body of the first liquid 1 is divided so that at least one sub-body is formed that comprises at least one conduit 36 connected to at least one reservoir 32, 34. The conduit 36 and reservoir 32,34 may be configured so that in use a liquid can be driven through the conduit 36 to or from the reservoir 32,34. The conduit 36 will typically have an elongate form when viewed perpendicularly to the first substrate 11. The reservoirs 32, 34 will typically be circular or at least have a lateral dimension that is larger than a width of the conduit 36. In the particular example shown, a T-shaped conduit 36 is provided that connects two source reservoirs 32 and 34 to a sink reservoir 34. Flow is driven in use, e.g. by Laplace pressure, hydrostatic pressure and/or pumping of material into the reservoirs 32, from the source reservoirs 32 to the sink reservoir 34.

Figure 16:
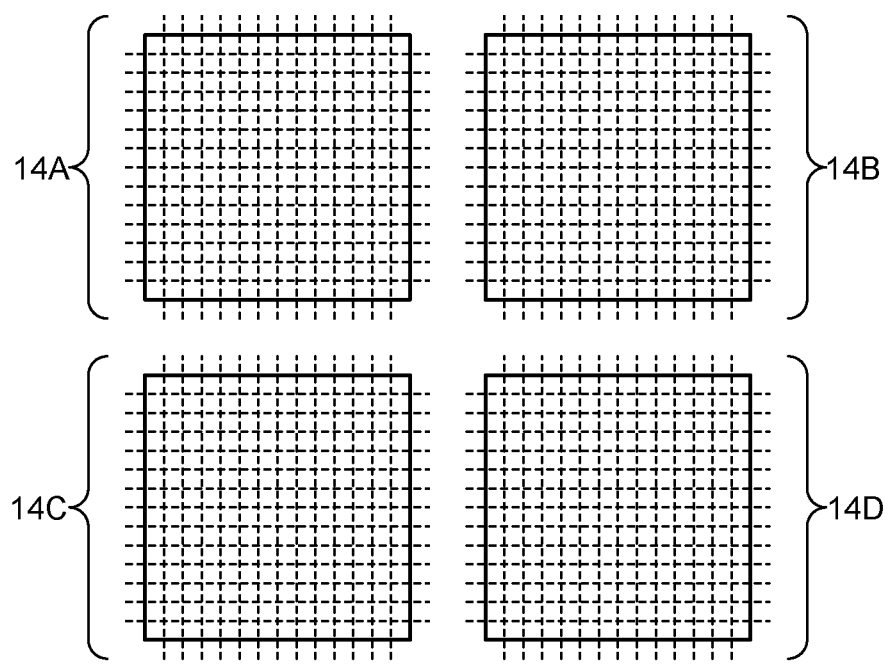
FIG. 16 depicts a scheme for creating multiple sets of sub-bodies of a first liquid having different compositions relative to each other by creating plural continuous bodies of the first liquid and subsequently dividing each of the continuous bodies to create sub-bodies.

In embodiments of the disclosure the continuous body of the first liquid 1 is formed by depositing the first liquid 1 onto the first substrate 11 by ejecting the first liquid 1 from an injection member while moving the injection member over the first substrate 11 to define the shape of the continuous body of the first liquid. This approach may be used for example when forming a continuous body of the first liquid 1 that is laterally constrained predominantly by surface tension (rather than by walls). In one such embodiment, as depicted in FIG. 16, a plurality of continuous bodies of a first liquid 1 are formed at different locations on the same first substrate 11. Each of the continuous bodies of the first liquid 1 is held in place by surface tension (interfacial forces). The provision of separate initial continuous bodies of the first liquid 1 allow the separate bodies to have different initial compositions relative to each other. Multiple respective sets of sub-bodies can be created in which the sub-bodies of each set are subjected to the same initial conditions, but the sub-bodies of different sets are subjected to different initial conditions. For example, in a case where biological material such as living cells is provided in each of the initial continuous bodies of the first liquid 1, different drugs could be added to two or more of the initial continuous bodies before they are divided into sub-bodies. In the particular example of FIG. 16, four continuous bodies of the first liquid 1 are provided (large squares depicted by solid lines). Each of the four continuous bodies are divided along the broken lines to form separate sets of sub-bodies 14A-D in four square arrays. In an embodiment, the four sets of sub-bodies 14A-D are provided by forming four continuous bodies of identical composition containing living cells. Different drugs are then added to each of the four continuous bodies of identical composition, optionally after the living cells have been allowed to adhere to the first substrate 11. The four continuous bodies are divided up to form the four sets of sub-bodies 14A-D and observed at a later time to assess the effect of the different drugs on the cells.

Figure 17:
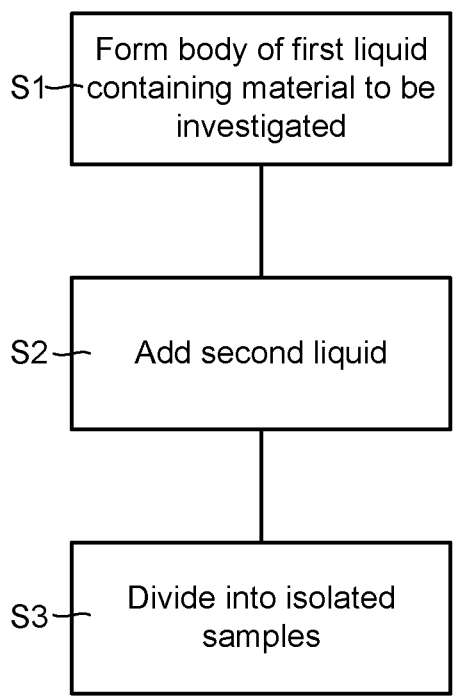
FIG. 17 is a flow chart describing the framework of a method of manufacturing a microfluidic arrangement for testing biological material.

In an embodiment, the manufactured microfluidic arrangement comprises a plurality of isolated samples that are used for investigating a material of interest. The framework of a method of investigation is depicted schematically in FIG. 17. In step S1, the continuous body of the first liquid 1 is formed and arranged to contain the material to be investigated. The material to be investigated is provided in the continuous body of the first liquid 1 prior to division of the continuous body to provide the sub-bodies. In step S2, the second liquid is added. In step S3, the continuous body is divided into the plurality of sub-bodies. The process of dividing the continuous body into the sub-bodies generates a plurality of isolated samples that each contain a portion of the material to be investigated without the material to be investigated needing to be added individually to each sample, which would be very time consuming, particularly where large numbers of the sub-bodies are created and/or where the sub-bodies are very small.

In an embodiment, the material to be investigated comprises biological material (such as cells, DNA, proteins, etc.). In an embodiment, the biological material comprises adherent living cells. Methods of embodiments of the present disclosure are particularly advantageous in this context because they allow adhered living cells to be treated en masse after they have been allowed to adhere to a substrate, and divided into plural isolated samples later on. This is not possible using prior art approaches and saves considerable time and system complexity, particularly where it is desired to create large numbers of isolated samples.

Figure 18:
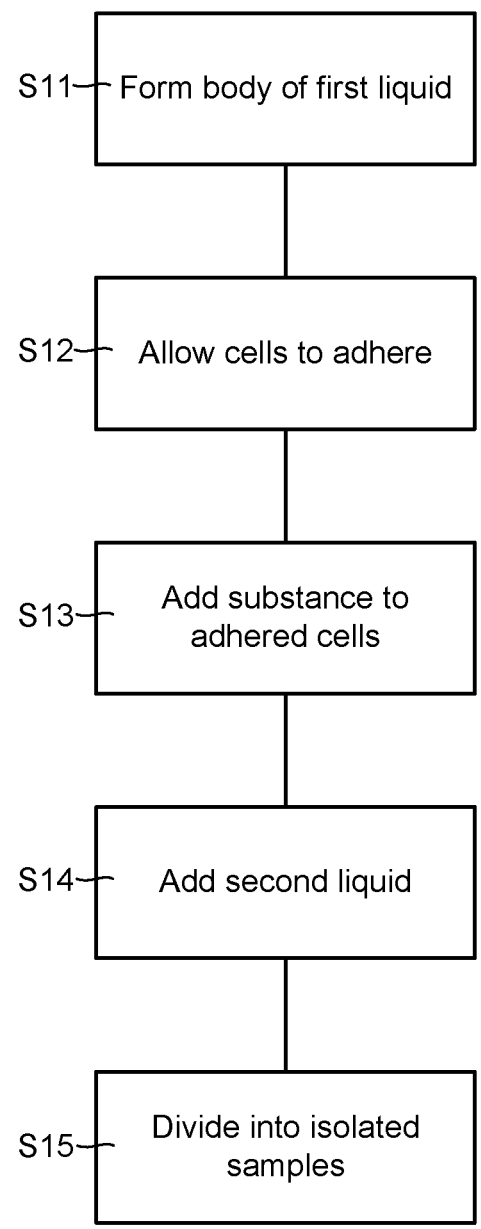
FIG. 18 is a flow chart describing the framework of a method of manufacturing a microfluidic arrangement for testing samples containing adherent living cells and a test substance.

FIG. 18 depicts the framework of a method applicable to handling adherent living cells. In step S11, the continuous body of the first liquid 1 is formed and arranged to contain the adherent living cells. In step S12, at least a portion of the adherent living cells, optionally a majority of the adherent living cells, are allowed to adhere to the first substrate 11 (this may be achieved for example by leaving the cells overnight in appropriate incubation conditions). When the cells are adhered to the first substrate 11 to a desired extent, the first liquid 1, which in this case may comprise suitable growth media, may optionally be poured off to leave a thin film of the first liquid 1 before moving on to step S13. In step S13, a test substance (e.g. a drug) is added to the continuous body of the first liquid 1 (which may be a thin film after the pouring off described above) containing the adhered living cells. An excess of the test substance may be optionally poured off at this stage to leave a thin film of first liquid 1 (containing the adhered cells, remnants of the growth media and the test substance). In step S14, the second liquid 2 is added. In step S15, the continuous body of the first liquid 1 is divided into the plurality of sub-bodies. The process of dividing the continuous body into the sub-bodies generates a plurality of isolated samples that each contain adhered living cells and a test substance that was added after the cells had adhered, without the test substance having needed to be added individually to each sample.

Figure 19:
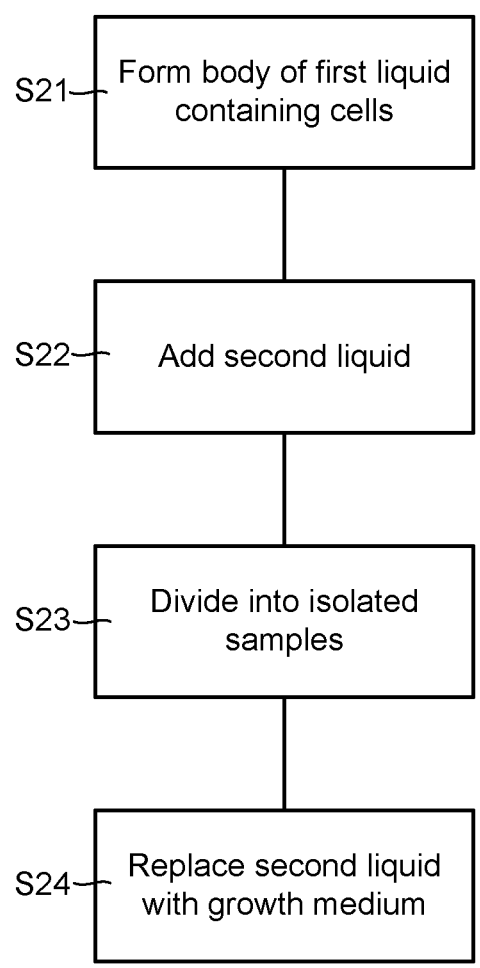
FIG. 19 is a flow chart describing the framework of a method of manufacturing a microfluidic arrangement for growing cell populations in groups.

FIG. 19 depicts the framework of a further method applicable to forming isolated samples containing living cells. In step S21, a continuous body of the first liquid 1 is formed and arranged to contain living cells, optionally adherent living cells. Step S21 may be identical to S11 discussed above. Step S21 may also comprise steps corresponding to either or both of steps S12 and S13 discussed above, so that adherent living cells may be allowed to adhere to the first substrate 11 and/or a test substance (e.g. a drug) may be applied to the adhered living cells. In step S22, the second liquid 2 is added. In step S23, the continuous body is divided into the plurality of sub-bodies. In step S24, the second liquid 2 is removed (e.g. by pouring off or syringing). The first liquid 1 may also be removed at this stage. Growth medium is then added to cover the first substrate 11. The inventors have found that the dividing lines separating the sub-bodies of the first liquid 1 when they are initially formed underneath the second liquid 2 continue to act as barriers to movement of cells even when the first liquid 1 and second liquid 2 have been removed and replaced by growth medium. Without wishing to be bound by theory, it is believed that the surface of the first substrate 11 is modified and/or residues of the first liquid 1 and/or the second liquid 2 are left behind and cause this effect. The result conveniently allows cell populations to be cultured in regions that are isolated from each other, thereby allowing multiple studies of individual populations of cells to be conducted efficiently in parallel. For example, where the sub-bodies initially contained only a single cell, the resulting cell population would all originate from the same single cell.

In an embodiment, the above methods are adapted to implement studies of single cells, or single molecules, or single proteins. This can be done for example by providing a concentration of living cells, molecules of interest, or proteins of interest, in the initial continuous body of the first liquid 1 that is low enough that the mean occupancy of each sub-body created by dividing the continuous body is less than one cell/molecule/protein of interest. In this way, many sub-bodies will be created that contain one and only one cell/molecule/protein of interest. This approach is considerably quicker than alternative approaches requiring individual deposition of cells/molecules/proteins of interest into separate wells after the wells have been created (e.g. in a microwell plate).

Figure 20:
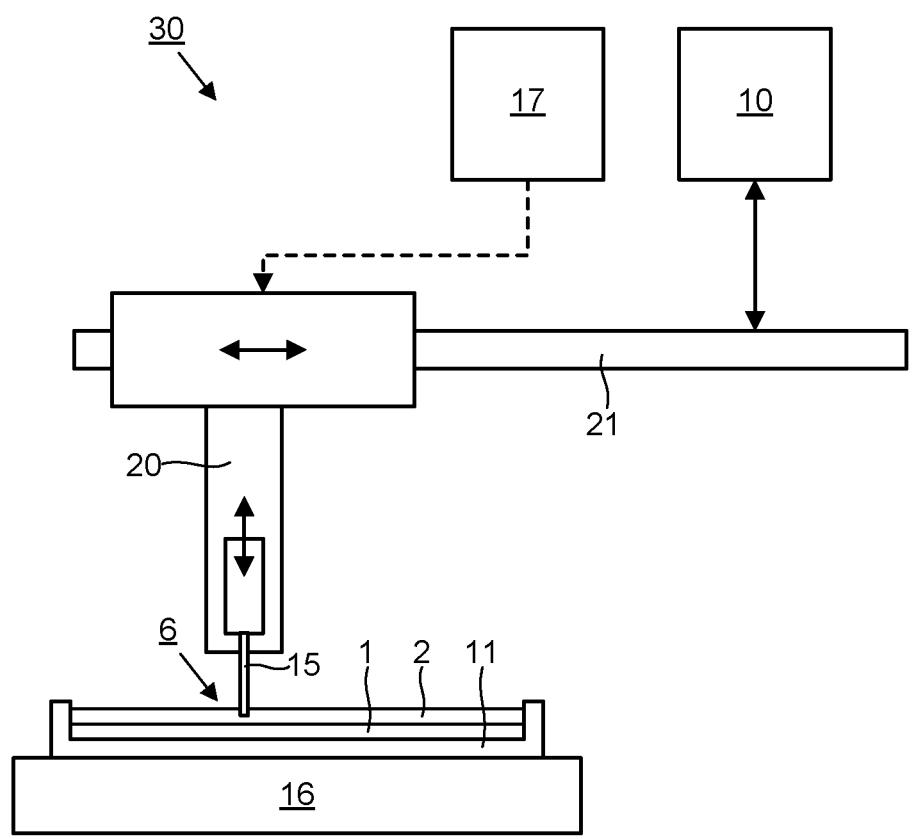
FIG. 20 depicts an apparatus for manufacturing a microfluidic arrangement according to embodiments of the disclosure involving pumping of separation fluid out of a distal tip of an injection member.
Figure 21:
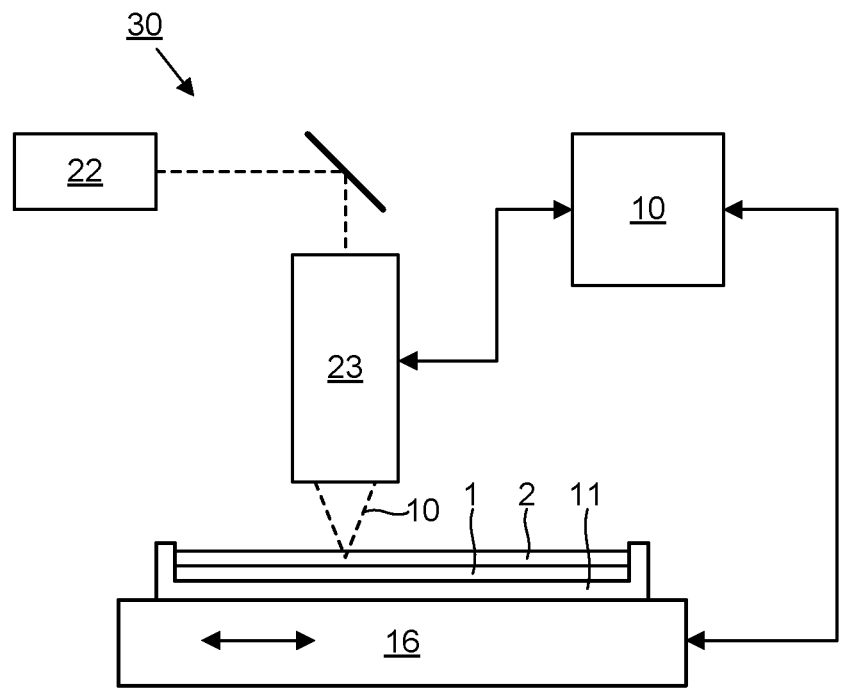
FIG. 21 depicts an apparatus for manufacturing a microfluidic arrangement according to embodiments of the disclosure involving use of a laser beam to propel the separation fluid through the firs liquid and into contact with the substrate.

FIGS. 20 and 21 depict example apparatus 30 for performing methods according to embodiments of the present disclosure. The apparatus 30 are thus configured to manufacture a microfluidic arrangement. The apparatus 30 comprises a substrate table 16. The substrate table 16 holds a substrate 11. A continuous body of first liquid 1 is provided in direct contact with the substrate 11. A second liquid 2 is provided in direct contact with the first liquid 1. The second liquid 2 covers the first liquid 1.

A pattern forming unit is provided that propels a separation fluid 3 through the first liquid 1 and into contact with the substrate 11 along all of the selected path 4. The propulsion of the separation fluid 3 may be performed using any of the methods described above with reference to FIGS. 1-19.

In the example of FIG. 20, the apparatus 30 propels the separation fluid 3 by pumping the separation fluid 3 out of a distal tip 6 of an injection member 15. The apparatus 30 of FIG. 20 comprises an injection system. The injection system is configured to pump separation fluid 3 out of the distal tip 6 of the injection member 15. The injection member 15 may comprise a lumen and the separation fluid 3 may be pumped along the lumen to the distal tip 6. In an embodiment, the separation fluid 3 is ejected from the distal tip 6 while the distal tip 6 is moved over the substrate 11 according to the geometry of the selected path 4. The injection system comprises the injection member 15 and a pumping system 17. In use, the pumping system 17 will comprise a reservoir containing the separation fluid 3, conduits for conveying the separation fluid 3 from the reservoir to the lumen of the injection member 15, and a mechanism for pumping the separation fluid 3 through the lumen and out of the distal tip 6 of the injection member 15.

In an embodiment, the apparatus 30 is configured to maintain a small but finite separation between the distal tip 6 of the injection member 15 and the substrate 11 while the injection member 15 is moved over the substrate 11. This is beneficial at least where the microfluidic arrangement is to be used for cell-based studies, which would be affected by any scratching or other modification of the surface that might be caused were the injection member 15 to be dragged over the substrate 11 in contact with the substrate 11. Any such modifications could negatively affect optical access and/or cell compatibility. In an embodiment, this is achieved by mounting the injection member 15 slideably in a mounting such that a force from contact with the substrate 11 will cause the injection member 15 to slide within the mounting. Contact between the injection member 15 and the substrate 11 is detected by detecting sliding of the injection member 15 relative to the mounting. When contact is detected, the injection member 15 is pulled back by a small amount (e.g. 20-150 microns) before the injection member 15 is moved over the substrate 11 (without contacting the substrate 11 during this motion). This approach to controlling separation between the distal tip 6 and the substrate 11 can be implemented cost effectively in comparison to alternatives such as the capacitive/inductive methods used in 3D printers, or optical based sensing techniques. The approach also does not require a conductive surface to be provided.

The injection system, or an additional injection system configured in a corresponding manner, may additionally provide the initial continuous body of the first liquid 1 in direct contact with the substrate 11 by ejecting the first liquid 1 through a distal tip of an injection member while moving the injection member over the substrate 11 to define the shape of the continuous body of the first liquid 1. In embodiments, the injection system or additional injection system may further be configured to controllably extract the first liquid 1, for example by controllably removing excess first liquid by sucking the liquid back through an injection member.

In an embodiment, the apparatus 30 comprises an application system for applying or removing the second liquid 2 (comprising for example a reservoir for holding the second liquid, an output/suction nozzle positionable above the substrate 11, and a pumping/suction mechanism for controllably pumping or sucking the second liquid 2 to/from the reservoir from/to the substrate 11 through the output/suction nozzle). In other embodiments, the second liquid 2 is applied manually.

The apparatus 30 of FIG. 20 further comprises a controller 10. The controller 10 controls movement of the injection member 15 over the substrate 11 during the propulsion of the separation fluid 3 onto the selected path on the substrate 11 (and, optionally, during forming of the continuous body of the first liquid 1). In an embodiment, the apparatus 30 comprises a processing head 20 that supports the injection member 15. The processing head 20 is configured such that the injection member 15 can be selectively advanced and retracted. In an embodiment, the advancement and retraction is controlled by the controller 10, with suitable actuation mechanisms being mounted on the processing head 20. A gantry system 21 is provided to allow the processing head 20 to move as required. In the particular example shown, left-right movement within the page is illustrated but it will be appreciated that the movement can also comprise movement into and out of the page as well as movement towards and away from the substrate 11 (if the movement of the injection member 15 provided by the processing head 20 itself is not sufficiently to provide the required upwards and downwards displacement of the injection member 15).

FIG. 21 depicts an apparatus 30 configured to propel a portion of the second liquid 2 towards the selected path by locally coupling energy into a region containing or adjacent to the portion of the second liquid 2. The apparatus of FIG. 21 may be configured to perform any of the methods described above with reference to FIGS. 6-10. The apparatus 30 comprises a laser source 22 (e.g. a sub-picosecond pulsed laser, as described above) and an optical projection system 23 configured to focus a beam provided by the laser source 22 onto a desired location. In an embodiment, the optical projection system 23 comprises a scanner for scanning a focussed laser spot along a scanning path following the geometry of the selected path 4. The scanner may be controlled by a controller 10. In an embodiment, the substrate table 16 is moved relative to the optical projection system 23 to provide, optionally in combination with scanning provided by the scanner, the scanning of the laser spot along the scanning path. The scanner may scan the spot along a first axis while the substrate table is moved along a second axis, perpendicular to the first axis, for example. Movement of the substrate table 16 may be controlled by the controller 10. Alternatively, a mask may be used to project a patterned radiation beam onto the substrate 11, a pattern of the beam corresponding to at least a portion of the selected path 4 on the substrate 11.

As mentioned in the introductory part of the description, it has been observed that alternative approaches which involve contact of a solid member with the selected path (e.g. a stylus that is scraped along the selected path to allow the second liquid to replace the first liquid along the selected path) can have a significant risk of producing sub-bodies that are incompletely separated from each other. For example, it has been observed that in arrays of sub-bodies produced using the alternative approach a small subset of the sub-bodies are found to be connected together. FIG. 22 depicts images of connections between sub-bodies of liquid (referred to as "chambers") produced using such an alternative approach. In this particular case, an array of square sub-bodies (chambers) were produced.

In the examples described above, the continuous body of the first liquid 1 and the overlying layer of second liquid 2 are provided before the separation fluid 3 is propelled through the first liquid 1 to form sub-bodies 7. In some embodiments, this is not the case, at least at an initial stage of the propelling of the separation fluid 3. In such embodiments, as depicted schematically in FIGS. 23 and 24, the separation fluid comprises (e.g. consists of) a liquid having the same composition as the second liquid 2. The providing of the second liquid 2 in direct contact with the continuous body of first liquid 1 and covering the continuous body of first liquid 1 comprises, after the continuous body of the first liquid 1 in direct contact with the first substrate 11 has been provided, propelling the separation fluid 3 through the first liquid 1 and into contact with the first substrate 11 along at least a portion of the selected path while a portion 50A of an upper interface of the first liquid 1 is not yet in contact with the second liquid 2. This situation is depicted in FIG. 23. The separation fluid 3 is propelled out of the distal tip 6 of an injection member and onto the selected path 4 on the first substrate 11 as indicated by the vertical arrow. Excess separation fluid 3 then moves up and outwards and starts to cover the upper interface of the first liquid 1 as indicated by the curved arrows. At the point in time depicted in FIG. 23, a portion 50B of the upper interface of the first liquid is covered by the advancing separation fluid 3 (which may also now be considered as a portion of the second liquid 2) while the portion 50A is in contact with air. The propelling of the separation fluid 3 continues until the separation fluid 3 forms a layer of second liquid 2 in direct contact with the continuous body of first liquid 1 and covering the continuous body of first liquid 1, as depicted in FIG. 24. At the stage shown in FIG. 24, no portion of the upper interface of the first liquid 1 is in contact with air.

In some embodiments, a separation fluid 3 is propelled through the first liquid 1 in a continuous process (i.e. without interruption) for at least a portion of the selected path 4. For example, separation fluid 3 may be propelled continuously out of a distal tip 6 of an injection member (e.g. by pumping at a continuous rate) while the distal tip 6 is moved over a portion of the selected path (e.g. in a straight line downwards as depicted in FIG. 3 or along one of the vertical solid line arrows in FIG. 14). In other embodiments, the propelling of the separation fluid 3 comprises intermittent propulsion of portions of the separation fluid 3 during at least a portion of the displacing of the first liquid 1 away from the selected path 4. For example, the separation fluid 3 may be propelled intermittently during the displacement of the first liquid 1 away from the selected path 4 along the portion of the selected path 4 shown in FIG. 3 or along any one of the portions of the selected path represented by the vertical solid line arrows in FIG. 14. In such embodiments, the intermittent propulsion may be such that the first liquid 1 is nevertheless displaced away from the selected path 4 so as to cause the selected path 4 to contact the second liquid 2 along a continuous line (e.g. along all of each of one or more of the vertical lines in FIGS. 3 and 14 referred to above). This may be achieved for example by arranging for different portions of the separation fluid 3 that are intermittently propelled towards the first substrate 11 (i.e. propelled at different times relative to each other) to be propelled into contact with the selected path in overlapping regions. Thus, an impact region on the first substrate 11 associated with one portion of propelled separation fluid 3 will overlap with the impact region on the first substrate 11 associated with at least one other portion of propelled separation fluid 3 (typically propelled at a slightly different time, for example after a head that is driving the propulsion has moved a short distance relative to the first substrate 11). The possibility of using intermittent propulsion opens up a wider range of possible mechanisms for driving the propulsion, such as piezoelectric mechanisms.

Alternative embodiments of the disclosure are described in the following numbered clauses.

1. A method of manufacturing a microfluidic arrangement, comprising:
   providing a continuous body of a first liquid in direct contact with a first substrate;
   providing a second liquid in direct contact with the continuous body of first liquid and covering the continuous body of first liquid; and
   propelling a separation fluid, immiscible with the first liquid, through at least the first liquid and into contact with the first substrate along all of a selected path on the surface of the first substrate, thereby displacing first liquid that was initially in contact with all of the selected path away from the selected path, the selected path being such that the continuous body of the first liquid is divided to form a single sub-body of first liquid separated from the rest of the continuous body of first liquid by the second liquid or a plurality of sub-bodies of first liquid separated from each other by the second liquid, wherein:
   for each of one or more of the sub-bodies, a sub-body footprint represents an area of contact between the sub-body and the first substrate and all of a boundary of the sub-body footprint is in contact with a closed loop of the selected path surrounding the sub-body footprint.
2. The method of clause 1, wherein the first liquid, second liquid and first substrate are configured such that each boundary of a sub-body footprint that is all in contact with a closed loop of the selected path is pinned in a static configuration by interfacial forces.
3. The method of clause 1 or 2, wherein the separation fluid immiscible with the first liquid comprises one or more of the following: a gas, a liquid, a liquid having the same composition as the second liquid, a portion of the second liquid provided before the propulsion of the separation fluid through the first liquid.
4. The method of any preceding clause, wherein for each of one or more of the sub-body footprints having a boundary that is all in contact with a closed loop of the selected path, the boundary comprises at least one straight line portion.
5. The method of any preceding clause, wherein at least a sub-set of the sub-body footprints that each have a boundary that is all in contact with a closed loop of the selected path tessellate with respect to each other.
6. The method of any preceding clause, wherein the separation fluid is propelled onto the selected path on the first substrate by pumping the separation fluid from a distal tip of an injection member while moving the distal tip relative to the first substrate.
7. The method of clause 6, wherein the distal tip is moved through the second liquid but not the first liquid while propelling the separation fluid onto the selected path on the first substrate, for at least a portion of the selected path.

8. The method of clause 6, wherein the distal tip is moved through both of the second liquid and the first liquid while propelling the separation fluid onto the selected path on the first substrate, for at least a portion of the selected path.
9. The method of clause 7 or 8, wherein at least a portion of the distal tip of the injection member is configured to be more easily wetted by the second liquid than the first liquid.
10. The method of any preceding clause, wherein:
the separation fluid comprises a portion of the second liquid; and
the portion of the second liquid is propelled towards the selected path on the first substrate by locally coupling energy into a region containing or adjacent to the portion of the second liquid to be propelled towards the selected path on the first substrate.
11. The method of clause 10, wherein the local coupling of energy is achieved using a focussed beam of electromagnetic radiation or ultrasound.
12. The method of clause 11, wherein a focus of the beam is scanned along a scanning path based on the geometry of the selected path.
13. The method of clause 11 or 12, wherein energy from the beam absorbed in the first substrate causes the first liquid to be locally forced away from the first substrate along the selected path, the second liquid moving into contact with the first substrate where the first liquid has been forced away.
14. The method of any of clauses 11-13, wherein:
the first substrate comprises a first base layer and a first intermediate absorbing layer between the first base layer and the first liquid;
a beam absorbance per unit thickness of the first intermediate absorbing layer is higher than a beam absorbance per unit thickness of the first base layer; and
energy from the beam absorbed in the first intermediate absorbing layer causes the first liquid to be locally forced away from the first substrate along the selected path, the second liquid moving into contact with the first substrate where the first liquid has been forced away.
15. The method of any of clauses 11-14, wherein a focus of the beam is positioned within the first substrate while the portion of the second liquid is propelled towards the selected path on the first substrate.
16. The method of any of clauses 11-14, wherein a focus of the beam is positioned within the second liquid while the portion of the second liquid is propelled towards the selected path on the first substrate.
17. The method of clause 16, wherein the beam propels the second liquid by causing cavitation in the second liquid.
18. The method of any of clauses 11-14, wherein a focus of the beam is positioned within the first liquid while the portion of the second liquid is propelled towards the selected path on the first substrate.
19. The method of clause 18, wherein the beam propels the second liquid by causing cavitation in the first liquid, the cavitation causing the first liquid to be locally forced away from the first substrate, the second liquid moving into contact with the first substrate where the first liquid has been forced away.
20. The method of any of clauses 11-14, further comprising a second substrate facing at least a portion of the first substrate and in contact with liquid, such that there is a continuous liquid path between the second substrate and the first substrate.
21. The method of clause 20, wherein energy from the beam absorbed in either or both of the second substrate and liquid adjacent to the second substrate causes the second liquid to be locally forced away from the second substrate, thereby providing the propulsion of the second liquid towards the selected path on the first substrate.
22. The method of clause 20 or 21, wherein:
the second substrate comprises a second base layer and a second intermediate absorbing layer between the second base layer and the second liquid;
a beam absorbance per unit thickness of the second intermediate absorbing layer is higher than a beam absorbance per unit thickness of the second base layer;
energy from the beam absorbed in the second intermediate absorbing layer causes the second liquid to be locally forced away from the second substrate, thereby providing the propulsion of the second liquid towards the selected path on the first substrate.
23. The method of any of clauses 20-22, wherein a focus of the beam is positioned within the second liquid while the portion of the second liquid is propelled towards the selected path on the first substrate.
24. The method of any of clauses 20-23, wherein the second substrate floats on liquid in contact with the second substrate.
25. The method of any of clauses 11-24, wherein:
a layer of a third liquid is provided above the second liquid;
a beam absorbance per unit thickness of the third liquid is higher than a beam absorbance per unit thickness of the second liquid; and
energy from the beam absorbed in the third liquid causes the second liquid to be locally propelled towards the selected path on the first substrate.
26. The method of any preceding clause, wherein the second liquid is denser than the first liquid.
27. The method of any preceding clause, wherein:
a material to be investigated is provided in the continuous body of the first liquid; and the division into sub-bodies generates a plurality of isolated samples that each contain a portion of the material to be investigated.
28. The method of clause 27, wherein the material to be investigated comprises biological material.
29. The method of clause 28, wherein the biological material comprises adherent living cells.
30. The method of clause 29, wherein at least a portion of the adherent living cells are allowed to adhere to the substrate before the continuous body of the first liquid is divided into the sub-bodies.
31. The method of clause 30, wherein:
a test substance is added to the continuous body of the first liquid after at least a portion of the adherent living cells have adhered to the substrate; and
the division into the sub-bodies is performed after the test substance has been added to the continuous body of the first liquid.
32. The method of clause 31, wherein the test substance comprises a drug.
33. The method of any of clauses 27-32, wherein the second liquid is replaced with growth medium after the division into the sub-bodies.
34. The method of any of clauses 27-33 wherein the biological material comprises living cells at a concentration such that a mean average occupancy of each sub-body is less than one living cell, or molecules of interest at a concentration such that a mean average occupancy of each sub-body is less than one molecule of interest.

35. The method of any preceding clause, wherein the continuous body of the first liquid is formed on the substrate before the second liquid is brought into contact with the first liquid.

36. The method of any preceding clause, wherein the continuous body of the first liquid is laterally constrained predominantly by surface tension.

37. The method of any preceding clause, wherein the continuous body of the first liquid is in direct contact exclusively with a substantially planar portion of the substrate and the second liquid.

38. The method of any preceding clause, wherein the forcing of the second liquid through the first liquid comprises the following steps in order:
dividing the continuous body of the first liquid symmetrically into two sub-bodies of equal volume; and
repeatedly dividing each sub-body formed by a preceding dividing step symmetrically into two further sub-bodies of equal volume.

39. The method of any preceding clause, wherein the first liquid is displaced away from the selected path without any solid member contacting the selected path directly and without any solid member contacting the selected path via a globule of liquid held at a tip of the solid member.

40. A microfluidic arrangement manufactured using the method of any preceding clause.

41. An apparatus for manufacturing a microfluidic arrangement, comprising:
a substrate table configured to hold a substrate on which a continuous body of a first liquid is provided in direct contact with a substrate, and a second liquid is provided in direct contact with the first liquid and covering the first liquid; and
a pattern forming unit configured to propel a separation fluid, immiscible with the first liquid, through at least the first liquid and into contact with the substrate along all of a selected path on the surface of the substrate, thereby displacing first liquid that was initially in contact with all of the selected path away from the selected path, the selected path being such that the continuous body of the first liquid is divided to form a single sub-body of first liquid separated from the rest of the continuous body of first liquid by the second liquid or a plurality of sub-bodies of first liquid separated from each other by the second liquid, wherein:
for each of one or more of the sub-bodies, a sub-body footprint represents an area of contact between the sub-body and the first substrate and all of a boundary of the sub-body footprint is in contact with a closed loop of the selected path surrounding the sub-body footprint.

The invention claimed is:

1. A method of manufacturing a microfluidic arrangement, comprising:
providing a continuous body of a first liquid in direct contact with a first substrate;
providing a second liquid in direct contact with the continuous body of first liquid and covering the continuous body of first liquid, the second liquid being immiscible with the first liquid; and
propelling a separation fluid, immiscible with the first liquid and miscible with the second liquid, through at least the first liquid and into contact with the first substrate along all of a selected path on the surface of the first substrate, thereby displacing first liquid that was initially in contact with all of the selected path away from the selected path without any solid member contacting the selected path directly and without any solid member contacting the selected path via a globule of liquid held at a tip of any solid member, the selected path being such that the continuous body of the first liquid is divided to form a single sub-body of first liquid separated from the rest of the continuous body of first liquid by the second liquid or a plurality of sub-bodies of first liquid separated from each other by the second liquid, wherein:
for each of the one or more sub-bodies, a sub-body footprint represents an area of contact between the sub-body and the first substrate, and all of a boundary of the sub-body footprint is in contact with a closed loop of the selected path surrounding the sub-body footprint; and
the first liquid, second liquid and first substrate are configured such that each boundary of a sub-body footprint that is all in contact with a closed loop of the selected path is pinned in a static configuration by interfacial forces, with the first liquid and the second liquid remaining in liquid form.

2. The method of claim 1, wherein the separation fluid immiscible with the first liquid comprises one or more of the following: a gas, a liquid, a liquid having the same composition as the second liquid, and a portion of the second liquid provided before the propulsion of the separation fluid through the first liquid.

3. The method of claim 1, wherein for each of one or more of the sub-body footprints having a boundary that is all in contact with a closed loop of the selected path, the boundary comprises at least one straight line portion.

4. The method of claim 1, wherein at least a sub-set of the sub-body footprints that each have a boundary that is all in contact with a closed loop of the selected path tessellate with respect to each other.

5. The method of claim 1, wherein the separation fluid is propelled onto the selected path on the first substrate by pumping the separation fluid from a distal tip of an injection member while moving the distal tip relative to the first substrate.

6. The method of claim 5, wherein the distal tip is moved through the second liquid but not the first liquid while propelling the separation fluid onto the selected path on the first substrate, for at least a portion of the selected path.

7. The method of claim 5, wherein the distal tip is moved through both of the second liquid and the first liquid while propelling the separation fluid onto the selected path on the first substrate, for at least a portion of the selected path.

8. The method of claim 6, wherein at least a portion of the distal tip of the injection member is configured to be more easily wetted by the second liquid than the first liquid.

9. The method of claim 1, wherein:
the separation fluid comprises a liquid having the same composition as the second liquid; and
the providing of the second liquid in direct contact with the continuous body of first liquid and covering the continuous body of first liquid comprises the following, after the continuous body of the first liquid in direct contact with the first substrate has been provided:
propelling the separation fluid through the first liquid and into contact with the first substrate along at least a portion of the selected path while a portion of an upper interface of the first liquid is not yet in contact with the second liquid, the propelling of the separation fluid continuing until the separation fluid forms a layer of second liquid in direct contact with the continuous body of first liquid and covering the continuous body of first liquid.

10. The method of claim 1, wherein:
the separation fluid comprises a portion of the second liquid;
the portion of the second liquid is propelled towards the selected path on the first substrate by locally coupling energy into a region containing or adjacent to the portion of the second liquid to be propelled towards the selected path on the first substrate; and
the local coupling of energy is achieved using a focused beam of electromagnetic radiation or ultrasound.

11. The method of claim 10, wherein a focus of the beam is scanned along a scanning path based on the geometry of the selected path.

12. The method of claim 10, wherein energy from the beam absorbed in the first substrate causes the first liquid to be locally forced away from the first substrate along the selected path, the second liquid moving into contact with the first substrate where the first liquid has been forced away.

13. The method of claim 10, wherein:
the first substrate comprises a first base layer and a first intermediate absorbing layer between the first base layer and the first liquid;
a beam absorbance per unit thickness of the first intermediate absorbing layer is higher than a beam absorbance per unit thickness of the first base layer; and
energy from the beam absorbed in the first intermediate absorbing layer causes the first liquid to be locally forced away from the first substrate along the selected path, the second liquid moving into contact with the first substrate where the first liquid has been forced away.

14. The method of claim 10, wherein a focus of the beam is positioned within the first substrate while the portion of the second liquid is propelled towards the selected path on the first substrate.

15. The method of claim 10, wherein a focus of the beam is positioned within the second liquid while the portion of the second liquid is propelled towards the selected path on the first substrate.

16. The method of claim 15, wherein the beam propels the second liquid by causing cavitation in the second liquid.

17. The method of claim 10, wherein a focus of the beam is positioned within the first liquid while the portion of the second liquid is propelled towards the selected path on the first substrate.

18. The method of claim 17, wherein the beam propels the second liquid by causing cavitation in the first liquid, the cavitation causing the first liquid to be locally forced away from the first substrate, the second liquid moving into contact with the first substrate where the first liquid has been forced away.

19. The method of claim 10, further comprising a second substrate facing at least a portion of the first substrate and in contact with liquid, such that there is a continuous liquid path between the second substrate and the first substrate.

20. The method of claim 19, wherein energy from the beam absorbed in either or both of the second substrate and liquid adjacent to the second substrate causes the second liquid to be locally forced away from the second substrate, thereby providing the propulsion of the second liquid towards the selected path on the first substrate.

21. The method of claim 19, wherein:
the second substrate comprises a second base layer and a second intermediate absorbing layer between the second base layer and the second liquid;
a beam absorbance per unit thickness of the second intermediate absorbing layer is higher than a beam absorbance per unit thickness of the second base layer;
energy from the beam absorbed in the second intermediate absorbing layer causes the second liquid to be locally forced away from the second substrate, thereby providing the propulsion of the second liquid towards the selected path on the first substrate.

22. The method of claim 19, wherein a focus of the beam is positioned within the second liquid while the portion of the second liquid is propelled towards the selected path on the first substrate.

23. The method of claim 19, wherein the second substrate floats on liquid in contact with the second substrate.

24. The method of claim 10, wherein:
a layer of a third liquid is provided above the second liquid;
a beam absorbance per unit thickness of the third liquid is higher than a beam absorbance per unit thickness of the second liquid; and
energy from the beam absorbed in the third liquid causes the second liquid to be locally propelled towards the selected path on the first substrate.

25. The method of claim 1, wherein the second liquid is denser than the first liquid.

26. The method of claim 1, wherein the propelling of the separation fluid comprises intermittent propulsion of portions of the separation fluid during at least a portion of the displacing of the first liquid away from the selected path.

* * * * *